(12) United States Patent
Bascomb et al.

(10) Patent No.: US 9,889,120 B2
(45) Date of Patent: Feb. 13, 2018

(54) COMBINATION DRUG THERAPIES FOR CANCER AND METHODS OF MAKING AND USING THEM

(71) Applicant: Vicus Therapeutics, LLC, Morristown, NJ (US)

(72) Inventors: Newell Bascomb, Hendersonville, NC (US); John Maki, Mendham, NJ (US); Fredric Young, Los Altos, CA (US)

(73) Assignee: Vicus Therapeutics, LLC, Hendersonville, NC (US)

( * ) Notice: Subject to any disclaimer, the term of this patent is extended or adjusted under 35 U.S.C. 154(b) by 0 days.

(21) Appl. No.: 15/405,109

(22) Filed: Jan. 12, 2017

(65) Prior Publication Data

US 2017/0202806 A1    Jul. 20, 2017

Related U.S. Application Data

(60) Provisional application No. 62/278,845, filed on Jan. 14, 2016.

(51) Int. Cl.
| | |
|---|---|
| *A61K 31/407* | (2006.01) |
| *A61K 31/133* | (2006.01) |
| *A61K 31/44* | (2006.01) |
| *A61K 45/06* | (2006.01) |
| *A61K 31/138* | (2006.01) |

(52) U.S. Cl.
CPC .......... *A61K 31/407* (2013.01); *A61K 31/138* (2013.01); *A61K 31/44* (2013.01); *A61K 45/06* (2013.01)

(58) Field of Classification Search
CPC ..... A61K 31/407; A61K 31/44; A61K 31/133
See application file for complete search history.

(56) References Cited

U.S. PATENT DOCUMENTS

| | | |
|---|---|---|
| 5,046,618 A | 9/1991 | Wood |
| 5,557,505 A | 9/1996 | Silva |
| 6,756,399 B2 | 6/2004 | Mulshine et al. |
| 6,830,153 B2 | 12/2004 | French et al. |
| 6,869,967 B2 | 3/2005 | Jeppesen et al. |
| 7,125,852 B2 | 10/2006 | Akiyama |
| 7,384,653 B2 | 6/2008 | Wright, IV et al. |
| 7,395,928 B2 | 7/2008 | Bertsch et al. |
| 2002/0008046 A1 | 1/2002 | Fuller et al. |
| 2004/0228802 A1 | 11/2004 | Chang et al. |
| 2005/0214223 A1 | 9/2005 | Bartholomaeus et al. |
| 2006/0135623 A1 | 6/2006 | Cutler |
| 2006/0138016 A1 | 6/2006 | Harper |
| 2007/0123499 A1 | 5/2007 | Teitelbaum et al. |
| 2008/0118560 A1 | 5/2008 | Juppo |
| 2009/0215852 A1 | 8/2009 | Bascomb et al. |
| 2011/0158983 A1 | 6/2011 | Bascomb et al. |

FOREIGN PATENT DOCUMENTS

| | | |
|---|---|---|
| EP | 2324821 A1 | 5/2005 |
| JP | 6-192073 | 7/1994 |
| JP | 2004-534050 A | 11/2004 |
| JP | 2006-96702 | 4/2006 |
| JP | 2006-213645 | 8/2006 |
| WO | WO 02/098398 A1 | 12/2002 |
| WO | WO200508699 A1 | 3/2005 |
| WO | WO2006102476 A2 | 9/2006 |
| WO | WO2006122162 A2 | 11/2006 |
| WO | WO2007100910 A2 | 9/2007 |
| WO | WO2008014471 A1 | 1/2008 |

OTHER PUBLICATIONS

Jones et al. Combination antiangiogenesis therapy with marimastat, captopril and fragmin in patients with advanced cancer. British Journal of Cancer, 2004, 91, 30-36.
Gasparini et al. Combination of antiatiogenic therapy with other anticancer therapies: results, challenges, and open questions. Journal of Clinical Oncology, vol. 23, No. 6, Feb. 20, 2005.
Bhounsule et al., Effect of captopri on oxyphenbutazone and ethanol-induced gastric lesions in rats. European Journal of Pharmacology (1990) 177:87-90.
Notice of Reasons for Rejection (including translation) for JP 2010-549887, dated Sep. 11, 2013, 17 pages.
Progress in Medicine (1997) 17(8):2247-2250.
Progress in Medicine (2002) 22(6):1484-1485.
Tomohiro et al., Effect of Teprenone on Gastric Mucosal Injury Induced by 5-Fluorouracil. Clinical Report (1995) 29(10):2587-2592.
Ushigima et al., Geranylgeranylacetone Protects Membranes against Nonsteroidal Anti-Inflammatory Drugs. Molecular Pharmacology (2005) 68(4):1156-1161.
Tochon-Danguy, Nathalie, Office Action issued in 2009221765, Australian Patent Office, dated Jul. 16, 2013.
Roques, Sarah E., Response filed Jun. 13, 2013 to Communication dated Dec. 3, 2012, European Patent Application No. EP09716791.0, European Patent Office.
Langer, Astrid, Office Action dated Jun. 23, 2014, European Patent Application No. EP09715791.0.

(Continued)

*Primary Examiner* — Yong L Chu
(74) *Attorney, Agent, or Firm* — Greer, Burns & Crain, Ltd.; Gregory P. Einhorn

(57) ABSTRACT

In alternative embodiments, provided are therapeutic combinations, pharmaceutical compositions, formulations, kits and devices for treating, preventing or ameliorating a tumor or a cancer, and methods and uses for treating, preventing or ameliorating a tumor or a cancer. In alternative embodiments, provided are therapeutic combinations, pharmaceutical compositions, formulations, kits and devices comprising: a beta adrenergic receptor antagonist (a "beta blocker") such as propranolol; a non-steroidal anti-inflammatory drug (a NSAID) such as etodolac; and, a sorafenib or NEXAVAR™ or equivalent thereof. In alternative embodiments, the therapeutic combinations further comprise an anti-cancer or anti-tumor antibody, a cytokine, and/or an additional chemotherapeutic agent. In alternative embodiments, the methods, uses, therapeutic combinations, pharmaceutical compositions, formulations, kits and devices are used for treating, preventing or ameliorating a hepatocarcinoma or hepatocellular carcinoma (HCC), an adenocarcinoma, a metastatic adenocarcinoma of the liver, or an advanced hepatocellular carcinoma.

23 Claims, 11 Drawing Sheets

(56) References Cited

OTHER PUBLICATIONS

Database WPI, Week 200416, Thomson Scientific, London GB, AN 2004-162175 & JP 2004 043391 A (EISAI Co. Ltd) Feb. 12, 2004.
McCarthy, et al. Risk factors associated with mucositis in cancer patients receiving 5-fluorouracil. Oral Oncology, 34, 1998, 484-490.
Nicholls et al. Ulceration of the tongue: a compilation of captopril therapy. Annals of Internal Medicine, May 1, 1981, vol. 94, Issue 6, p. 659.
Dorwald, Side Reactions in Organic Synthesis: A guide to successful synthesis design, Weinheim: Wiley-VCH, Verlag GmbH & Co. KGaA, 2005, Preface.
Si et al., Quality of gastric ulcer healing evaluated by endoscopic ultrasonography, World J. Gastroenterol. (2005) 11(22):3461-3464.
Benish et al., Perioperative use of Beta Blockers and COX-2 Inhibitors may improve immune competence and reduce the risk of tumor metastasis, Ann Surg. Oncol. (2008) 15(7):2042-2052.
Brophy, et al. Bioavailability of oral dexamethasone during high dose steroid therapy in neurological patients, Eur. J. Clinical Pharmacal. (1983) 24:103-108.
Fotherby, K. Bioavailability of orally aministered sex steroids used in oral contraception and hormone replacement therapy. Contraception (1996) 54:59-69.
Groning, et al. Threedimentional solubility parameters and their use in characterising the permeation of drugs through the skin. Pharmazie, (1996) 51:337-341.
Hidalgo-Aragones, et al. Pharmacokinetics of Oestrone-3-O-Sulphamate. J. Steroid Biochem. Mol. Biol. (1996) 58:611-617.
International Search Report for PCT/US2009/036205, dated May 7, 2009, 5 pages.
Johnson, Permeation of steroids through human skin. J. Pharm. Sci. (1995) 84:1144-1146.
Ou, Development and validation of an improved oxygen radical absorbance capacity assay using fluorescein as the fluorescent probe. J. Agric. Food Chem. (2001) 49(10): 4619-4626.
Rohatagi, Pharmacokinetic interaction between endogenous cortisol and exogenous corticosteroids. Pharmazie (1995) 50:610-613.
Written Opinion of the International Searching Authority for PCTUS2009/036205, dated May 7, 2009, 8 pages.
Supplementary European Search Report for EP 09716791.0, dated Jan. 4, 2012, 7 pages.
Extended Eruropean Search Report for EP 11185094.7, dated Dec. 15, 2011.
Tochon-Danguy, Patent Examination Report No. 1 for Australian Patent Application 2015207835, dated Apr. 19, 2016.
Tochon-Danguy, Examination report No. 2 for Australian Patent Application 2015207835, dated Mar. 23, 2017.
Nobuyo Kamijyo, Office Action for Japanese Patent Application 2014-038651, dated Jan. 26, 2016.
Nobuyo Kamijyo, Office Action for Japanese Patent Application 2014-038651, dated Jul. 21, 2016.
Brannon-Peppas et al., "Nanoparticle and targeted systems for cancer therapy." Advanced Drug Delivery Reviews, 2004, v 56, p. 1649-1659.
Liu et al., "A phase II study of BAY 43-9006 (Sorafenib) in patients with relapsed non-small cell lung cancer", Journal of Clinical Oncology, 2006, vol. 24, No. 18S.
Wood, "Managing side effects of sorafenib and sunitinib." Community Oncology, Sep. 2006, v 3, n 9, p. 558-562.
Wu et al., "Incidence and risk of hypertension with sorafenib in patients with cancer: a systematic review and meta-analysis." http://oncology.thelancet.com, Feb. 2008, v 9.

FIG. 3

Table 1. Potential Benefits of COX-2 and Adrenergic Inhibition in the Oncology Setting.

| COX-2 Inhibitors | Adrenergic Inhibitors |
|---|---|
| • Modulates inflammation / immunosuppression<br>  - Cytokines, chemokines, COX-2, MMPs, NK-kB, STAT3, AP-1, HIF-1alpha<br>  - note – celecoxib activates MEK/ERK/SNAIL and induces EMT<br>• Reduces infiltrating monocytes<br>• Prevents hypoxic upregulation of HIFalpha<br>• Down-regulates VEGF<br>• Inhibits apoptosis<br>• Reduces angiogenesis<br>• Reduces invasiveness<br>• Inhibits Wnt, increases E cadherin<br>• Inhibits RXR-alpha<br>• Inhibits iNOS<br>• Reduces osteoblastic metastases | • Reduces adrenergic push to TH2, restores balance towards TH1 response<br>• Blocks adrenergic suppression of NK cell activation<br>• Reverses stress-induced macrophage migration<br>• Attenuates VEGFR and HIFalpha expression<br>• Prevents neuroendocrine-induced cell migration and metastasis<br>• Reduces neurogenesis<br>• Reduces angiogenesis<br>• Reduces bone turnover (sympathetic regulation of osteoclasts and osteoblasts) |

AP-1=activator protein 1; COX=cyclooxygenase; EMT=epithelial-mesenchymal transition; ERK=extracellular signal-regulated kinases; HIF=hypoxia inducible factor; iNOS=inducible nitric oxide synthase; MEK1/2=mitogen-activated protein kinase; MMP=matrix metalloproteases; NK=natural killer; RXR=retinoid X receptor; STAT3=signal transducer and activator of transcription 3; TH=T-helper; VEGF=vascular endothelial growth factor; VEGFR=vascular endothelial growth factor receptor.

COMBINATION DRUG THERAPIES FOR CANCER AND METHODS OF MAKING AND USING THEM

RELATED APPLICATIONS

This application claims benefit of priority to U.S. Provisional Patent Application Ser. No. 62/278,845, filed Jan. 14, 2016. The aforementioned application is expressly incorporated herein by reference in its entirety and for all purposes.

FIELD OF THE INVENTION

This invention relates generally to medicine, pharmaceutical formulations and medical devices. In alternative embodiments, provided are therapeutic combinations, pharmaceutical compositions, formulations, kits and devices for treating, preventing or ameliorating a tumor or a cancer, and methods and uses for treating, preventing or ameliorating a tumor or a cancer. In alternative embodiments, provided are therapeutic combinations, pharmaceutical compositions, formulations, kits and devices comprising: a beta adrenergic receptor antagonist (a "beta blocker") such as propranolol; a non-steroidal anti-inflammatory drug (a NSAID) such as etodolac; and, a sorafenib or NEXAVAR™ or equivalent thereof. In alternative embodiments, the therapeutic combinations further comprise an anti-cancer or anti-tumor antibody, a cytokine, and/or an additional chemotherapeutic agent. In alternative embodiments, the methods, uses, therapeutic combinations, pharmaceutical compositions, formulations, kits and devices are used for treating, preventing or ameliorating a hepatocarcinoma or hepatocellular carcinoma (HCC), an adenocarcinoma, a metastatic adenocarcinoma of the liver, or an advanced hepatocellular carcinoma.

BACKGROUND

Chemotherapy is important in cancer treatment, but chemotherapy drugs act by damaging high proliferating cells, and damage to normal cells results in chemotherapy toxicities and side effects. Chemotoxicity can be seen most in actively dividing tissues such bone marrow, hair follicles and gastrointestinal mucosa. New approaches in cancer chemotherapeutics are needed to address these challenges.

SUMMARY

In alternative embodiments, provided are therapeutic combinations of therapeutic agents or drugs for an individual in need thereof comprising or consisting of:
(a)
(i) a beta adrenergic receptor antagonist (a "beta blocker");
(ii) a non-steroidal anti-inflammatory drug (a NSAID); and
(iii) a 4-[4-[[4-chloro-3-(trifluoromethyl)phenyl]carbamoylamino] phenoxy]-N-methyl-pyridine-2-carboxamide or a bioisostere thereof, or a sorafenib or NEXAVAR™ or any equivalent thereof;
(b) the therapeutic combination of therapeutic agents or drugs of (a), wherein the non-steroidal anti-inflammatory drug (a NSAID) comprises:
(i) a cyclooxygenase (COX) (or a prostaglandin synthase) inhibitor; or,
(ii) the COX inhibitor of (a), wherein the COX inhibitor comprises or consists of an etodolac or equivalent; a naproxen or equivalent; a celecoxib or equivalent; a rofecoxib or equivalent; a etoricoxib or equivalent; a valdecoxib or equivalent; a parecoxib or equivalent; a nabumetone or equivalent; a diclofenac (2-(2,6-dichloranilino) phenylacetic acid) or equivalent; or, a lumiracoxib or equivalent;
(c) the therapeutic combination of therapeutic agents or drugs of (a), wherein the beta adrenergic receptor antagonist (a beta blocker) comprises propranolol or equivalent, and optionally the propranolol is INDERAL™, AVLOCARDYL™, DERALIN™, DOCITON™, INDERALICI™, INNOPRAN XL™, or SUMIAL™; or
(d) the therapeutic combination of therapeutic agents or drugs of (a), wherein the therapeutic combination of an NSAID and beta blocker comprises or is a VT-122™ (Vicus Therapeutics, Morristown, N.J.).

In alternative embodiments, the etodolac is a LODINE™, LODINE SR™ or ECCOXOLAC™; or the celecoxib is CELEBREX™ or CELEBRA™; or the rofecoxib is VIOXX™, CEOXX™ or CEEOXX™; or the etoricoxib is ARCOXIA™, ALGIX™ or TAUXIB™; or the valdecoxib is BEXTRA™; the parecoxib is DYNASTAT™; the naproxen is XENOBID™, ALEVE™, ANAPROX™, MIRANAX™, NAPROGESIC™, NAPROSYN™, NAPRELAN™, PROXEN™ or SYNFLEX™; the nabumetone is RELAFEN™, RELIFEX™ or a GAMBARAN™; or, the diclofenac is FLECTOR PATCH™, VOLTAREN™, VOLTAROL™, DICLON™, DICLOFLEX DIFEN™, DIFENE™, CATAFLAM™, PENNSAID™, PANAMOR™, RHUMALGAN™, MODIFENAC™, ABITREN™, OLFEN™, VOVERAN™, ARTHROTEC™, DEDOLOR™, DEFLAMAT™, VETAGESIC™ or ZOLTEROL™.

In alternative embodiments, the therapeutic combination of therapeutic agents or drugs as provided herein further comprise an anti-cancer or anti-tumor antibody, wherein optionally the anti-cancer or anti-tumor antibody is an alemtuzumab, a brentuximab vedotin, a cetuximab, a gemtuzumab ozogamicin, an abritumomab tiuxetan, a nimotuzumab, an ofatumumab, a panitumumab, a rituximab, a tositumomab, or a trastuzumab.

In alternative embodiments, the therapeutic combination of therapeutic agents or drugs as provided herein further comprise a cytokine, wherein optionally the cytokine comprises an IL-2 or an interferon (IFN), and optionally the interferon is an alpha-IFN or a gamma-IFN;
and optionally the IL-2 is a recombinant IL-2, an aldesleukin, or a PROLEUKIN (Prometheus Laboratories), wherein optionally the IL-2, recombinant IL-2, or aldesleukin is dosages at about: 1 to 20, 2 to 10, 4 to 5, or 4.5 millions of IUs per cycle; or is dosaged for: 1 to 5, 2 to 4, or 3 cycles number of cycles of therapy.

In alternative embodiments, the therapeutic combination of therapeutic agents or drugs as provided herein further comprise a chemotherapeutic agent, wherein optionally the chemotherapeutic agent comprises a doxorubicin or a carboplatin, or comprises an inducer of apoptosis or a mitotic inhibitor or anti-microtubule inhibitor, or an alkylating agent, a nucleoside or nucleotide analog, or a topoisomerase inhibitor, or a glycopeptide antibiotic, or steroid receptor inhibitor, or a matrix metalloproteinase (MMP) inhibitor, or an mTOR (mammalian target of rapamycin) inhibitor, or a macrolide or a composition comprising a macrolide ring,
and optionally the inducer of apoptosis or a mitotic inhibitor or anti-microtubule inhibitor comprises or consists of a raltitrexed or equivalent, or TOMUDEX™; a doxorubicin or equivalent, or ADRIAMYCIN™; a fluorouracil or 5-fluorouracil or equivalent; a paclitaxel or equivalent, or TAXOL™ or ABRAXANE™; a docetaxel or equivalent, or TAXOTERE™; a larotaxel, tesetaxel or ortataxel or equivalent; an epothilone or an epothilone A, B, C, D, E or F or equivalent; an ixabepilone (also known as azaepothilone B) or equivalent, or BMS-247550™; a vincristine (also known as leurocristine) or equivalent, or ONCOVIN™; a vinblastin, vinblastine, vindesine, vinflunine, vinorelbine or NAVELBINE™ or equivalent; or, any combination thereof, and optionally the alkylating agent comprises or consists of a temozolomide, (TMZ) (TEMODAR™, TEMODAL™ or TEMCAD™), a cisplatin or equivalent; a cisplatinum or equivalent; a cis-diamminedichloridoplatinum(II) (CDDP) or equivalent; a carboplatin or equivalent; a oxaloplatin or equivalent; a cyclophosphamide (cytophosphane) or equivalent, or ENDOXAN™, CYTOXAN™, NEOSAR™ or REVIMMUNE™; a mechlorethamine or equivalent; a chlormethine or equivalent; a mustine or equivalent; a nitrogen mustard or equivalent; a chlorambucil or equivalent, or LEUKERAN™; or, a combination thereof, and optionally the topoisomerase inhibitor comprises or consists of an etoposide or equivalent, or EPOSIN™, ETOPOPHOS™, VEPESID™ or VP-16™; an amsacrine or equivalent; a topotecan or equivalent, or HYCAMTIN™; a teniposide or equivalent, or VUMON™ or VM-26™; an epipodophyllotoxin or equivalent; a camptothecin or equivalent; an irinotecan or equivalent, or CAMPTOSAR™; or, a combination thereof, and optionally the glycopeptide antibiotic comprises or consists of a bleomycin or equivalent or a bleomycin $A_2$ or $B_2$ or equivalent; a mitomycin or a mitomycin C or equivalent, a plicamycin (also known as mithramycin) or equivalent, or MITHRACIN™; or, a combination thereof, and optionally the steroid receptor inhibitor comprises or consists of an estrogen receptor modulator (a SERM), and optionally the estrogen receptor modulator comprises or consists of a tamoxifen or equivalent, or NOLVADEX™, ISTUBAL™ or VALODEX™, and optionally the steroid inhibitor or an anti-steroid comprises or consists of a finasteride or equivalent, or PROSCAR™, PROPECIA™, FINCAR™, FINPECIA™, FINAX™, FINAST™, FINARA™, FINALO™, PROSTERIDE™, GEFINA™, APPECIA™, FINASTERID IVAX™, FINASTERID or ALTERNOVA™, and optionally the macrolide or composition comprising a macrolide ring comprises or consists of a clarithromycin or equivalent, or BIAXIN™, KLARICID™, KLABAX™, CLARIPEN™, CLARIDAR™, FROMILID™ or CLACID™; an azithromycin or equivalent, or ZITHROMAX™, ZITROMAX™ or SUMAMED™; a dirithromycin or equivalent; an erythromycin or equivalent; a roxithromycin or equivalent, or ROXO™, SURLID™, RULIDE™, BIAXSIG™, ROXAR™, ROXIMYCIN™ or COROXIN™; a telithromycin or equivalent or KETEK™; a josamycin or equivalent; a kitasamycin or equivalent; a midecamycin or equivalent; oleandomycin or equivalent; a roxithromycin or equivalent, or ROXO™, SURLID™, RULIDE™, BIAXSIG™, ROXAR™, ROXIMYCIN™ or COROXIN™; a troleandomycin or equivalent; or a tylosin or equivalent; or, any combination thereof, wherein optionally the nucleoside or nucleotide analog comprises a cytarabine or cytosine arabinoside or CYTOSAR-U™ or DEPOCYT™, a gemcitabine or GEMZAR™;

wherein optionally the chemotherapeutic agent comprises a sorafenib or equivalent, or NEXAVAR™; a sunitinib or equivalent, or SUTENT™; an erlotinib or equivalent, or TARCEVA™; an imatinib or equivalent, or GLEEVEC™; a lapatinib or equivalent, or TYKERB™; a toceranib or equivalent, or PALLADIA™; a masitinib or equivalent, or MASIVET™, a bevacizumab or equivalent, or AVASTIN™; a trastuzumab or equivalent, or HERCEPTIN™; a cetuximab or equivalent, or ERBITUX™; a bevacizumab or equivalent, or AVASTIN™ or BIBW 2992; a gefitinib or equivalent, or IRESSA™; a ranibizumab or equivalent, or LUCENTIS™; a pegaptanib or equivalent, or MACUGEN™; a dasatinib or equivalent, or BMS-354825™; a sunitinib or equivalent, or SUTENT™; a pazopanib or equivalent; a nilotinib or equivalent, or TASIGNA™; a panitumumab or equivalent, or VECTIBIX™; a bandetinib or equivalent; a brivanib or equivalent, or E7080™; a thalidomide or equivalent, or THALOMID™; lenalidomide or equivalent, or REVLIMID™; a bortezomib or equivalent, or VELCADE™; disulfiram or equivalent, or ANTABUSE™ or ANTABUS™; or an epigallocatechin gallate (EGCG) or equivalent; a demecolcine, an etoglucid or elsamitrucin, a lonidamine, a lucanthone, a mitotane or a mitoguazone or equivalent; or any combination thereof.

In alternative embodiments, the therapeutic combination of therapeutic agents or drugs as provided herein further comprise a radiotherapy enhancing agent.

In alternative embodiments, the therapeutic combination of therapeutic agents or drugs as provided herein further comprise a proton pump inhibitor (a PPI), wherein optionally the proton pump inhibitor comprises or consists of a benzimidazole compound or structure, or an imidazopyridine compound or structure.

In alternative embodiments, the therapeutic combination of therapeutic agents or drugs as provided herein further comprise a radioactive particle or isotope; or a microscopic, radioactive glass microsphere, or a TheraSphere (THERASPHERE™); or a drug-eluting or a cancer drug-eluting particle, liposome or bead, or a doxorubicin-loaded drug-eluting bead, or a DC Bead®.

In alternative embodiments, the therapeutic combination of therapeutic agents or drugs as provided herein further comprise an adjuvant.

In alternative embodiments, two or more drugs of the therapeutic combination are formulated as separate compositions, or two or more drugs of the therapeutic combination are formulated into one composition or drug formulation (two or more drugs of the therapeutic combination are formulated together).

In alternative embodiments, the beta adrenergic receptor antagonist, or the beta blocker or equivalent, or the propranolol or equivalent; the non-steroidal anti-inflammatory drug, or the NSAID or equivalent, or the etodolac or equivalent; and a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are all formulated or packaged in different compositions or formulations, in a single formulation or package, or in paired combinations or packages, and optionally are all administered separately or are all administered together, and optionally the beta adrenergic receptor antagonist, the beta blocker or equivalent, or the propranolol or equivalent and the NSAID or equivalent, or the etodolac or equivalent, are administered or packaged together either in separate formulations or packages or a single formulation or package, and optionally a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are administered or packaged together either in separate formulations or packages or a single formulation or packages;

(b) the beta adrenergic receptor antagonist, or a beta blocker or equivalent, or a propranolol or equivalent; and the non-steroidal anti-inflammatory drug, or a NSAID or equivalent, or an etodolac or equivalent are formulated in different compositions or formulations, or, are formulated in the same composition or formulation, or are formulated together.

In alternative embodiments, one or two or more or all of the drugs of the therapeutic combination are packaged individually, or are packaged together, or packaged in any combination, in a single package, a plurality of packages or packettes, or packaged as a blister packet, lidded blister or blister card or packets, or a shrink wrap.

In alternative embodiments, the beta adrenergic receptor antagonist, or a beta blocker or equivalent, or a propranolol or equivalent; the non-steroidal anti-inflammatory drug, or a NSAID or equivalent, or an etodolac or equivalent; and the therapeutic agent for the treatment of cancer, are packaged individually in a single package, a plurality of packages or packettes, or a blister packet, lidded blister or blister card or packets, or a shrink wrap. In alternative embodiments, one or two or more or all of the drugs of the therapeutic combination are packaged together or in any combination in a single package, a plurality of packages or packettes, or a blister packet, lidded blister or blister card or packets, or a shrink wrap. In alternative embodiments, two, three or more or all of the drugs are released upon opening of the single package, plurality of packages or packettes, blister packet, lidded blister, blister card or packets or shrink wrap.

In alternative embodiments, the beta adrenergic receptor antagonist, or a beta blocker or equivalent, or a propranolol or equivalent; the non-steroidal anti-inflammatory drug, or a NSAID or equivalent, or an etodolac or equivalent; and the therapeutic agent for the treatment of cancer are packaged together in a single package, a plurality of packages or packettes, or a blister packet, lidded blister or blister card or packets, or a shrink wrap, and two or more or all of the drugs are released upon opening of the single package, plurality of packages or packettes, blister packet, lidded blister, blister card or packets or shrink wrap.

In alternative embodiments, one or two or more or all of the drugs of the therapeutic combination are formulated or manufactured as a parenteral formulation, an aqueous solution, a liposome, an injectable solution, a tablet, a pill, a lozenge, a capsule, a caplet, a patch, a spray, an inhalant, a powder, a freeze-dried powder, an inhalant, a patch, a gel, a geltab, a nanosuspension, a nanoparticle, a nanoliposome, a microgel, a pellet, a suppository or any combination thereof.

In alternative embodiments, one or two or more or all of the drugs of the therapeutic combination are formulated or manufactured together in one parenteral formulation, one aqueous solution, one liposome, one injectable solution, one freeze-dried powder, one feed, one food, one food supplement, one pellet, one lozenge, one liquid, one elixir, one aerosol, one inhalant, one adhesive, one spray, one powder, one freeze-dried powder, one patch, one tablet, one pill, one capsule, one gel, one geltab, one lozenge, one caplet, one nanosuspension, one nanoparticle, one nanoliposome, one microgel or one suppository.

In alternative embodiments: (a) the dosage of etodolac ranges from about 200 mg to 400 mg a day, or, about 10, 15, 20, 25, 30, 35, 40, 45, 50, 75, 80, 85, 90, 100, 150, 200, 250, 300, 350, 400, 450, 500, 600, 700, 800, 900 or 1000 mg or more; or, (b) the dosage of propranolol ranges from 10 to 320 mg per day based on heart rate and blood pressure of the individual, or, about 10, 15, 20, 25, 30, 35, 40, 45, 50, 75, 80, 85, 90, 100, 150, 200, 250, 300, 350, 400, 450, 500, 600, 700, 800, 900 or 1000 mg or more.

In alternative embodiments, the drug combination is packaged in dosages that match a chrono-dosing regimen to match an optimal dose for the time of day. In alternative embodiments, the beta adrenergic receptor antagonist or a beta blocker or equivalent, or a propranolol or equivalent; the non-steroidal anti-inflammatory drug or NSAID or equivalent, or etodolac or equivalent; and also optionally a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are packaged in dosages that match a chrono-dosing regimen to match an optimal dose for the time of day.

In alternative embodiments, the beta adrenergic receptor antagonist or beta blocker or equivalent or propranolol or equivalent; the non-steroidal anti-inflammatory drug or NSAID or equivalent or etodolac or equivalent; and also optionally a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are packaged in dosages that match a chrono-dosing regimen comprising:

(a) in the AM, 20 to 80 mg beta adrenergic receptor antagonist (a beta blocker), e.g., a propranolol or equivalent, 200 to 400 mg NSAID, e.g., an etodolac or equivalent;

in the afternoon, 10 to 20 mg beta blocker, optionally 200 mg NSAID, e.g., an etodolac or equivalent;

in the PM, 40 to 300 mg NSAID, optionally 10 to 20 mg propranolol; (b) in the AM 20 to 80 mg, e.g., 40 mg, beta adrenergic receptor antagonist (a beta blocker), e.g., a propranolol or equivalent, 200 to 400 mg NSAID, e.g., an etodolac or equivalent;

in the afternoon 10 to 40 mg, e.g., 20 mg, beta blocker, optionally 200 to 400 mg NSAID;

in the evening, 40 to 400 mg, e.g., 300 mg, NSAID, optionally 10 to 20 mg propranolol;

(c) in the AM 20 to 80 mg, e.g., 20, 30 or 40 mg, beta adrenergic receptor antagonist (a beta blocker), e.g., a propranolol or equivalent, 200 to 300 mg NSAID (e.g., etodolac or equivalent);

in the afternoon 10 to 80 mg, e.g., 20, 30 or 40 mg, beta blocker, 200 to 400 mg NSAID;

in the evening (in the PM) 40 to 400 mg, e.g., 300 mg, NSAID;

(d) in the AM 20 to 80 mg beta adrenergic receptor antagonist (a beta blocker), e.g., a propranolol or equivalent, 200 to 400 mg, e.g., 300 mg, NSAID (e.g., etodolac or equivalent); in the afternoon 20 to 40 mg beta blocker; in the evening (in the PM) 40 to 300 mg, NSAID; or (e) a dose escalation comprising a regimen of any of (a) to (d).

In alternative embodiments, the beta adrenergic receptor antagonist or beta blocker or equivalent or propranolol or equivalent; the non-steroidal anti-inflammatory drug or NSAID or equivalent or etodolac or equivalent; and also optionally a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are packaged in dosages that match a chrono-dosing regimen comprising:

Start: AM, 20 mg propranolol, 200 mg etodolac; afternoon, 10 mg propranolol, 200 mg etodolac; PM 400 mg etodolac, optionally 5 mg propranolol;

Dose Escalation 1: AM 40 mg propranolol, 200 mg etodolac; afternoon 20 mg propranolol, 200 mg etodolac; evening, 400 mg etodolac, optionally 10 mg propranolol;

Dose escalation 2: AM 80 mg propranolol, 200 mg etodolac; afternoon 40 mg propranolol, optionally 200 mg etodolac, evening 20 mg, etodolac.

In alternative embodiments, the beta adrenergic receptor antagonist or beta blocker or equivalent or propranolol or equivalent; the non-steroidal anti-inflammatory drug or NSAID or equivalent or etodolac or equivalent; and also optionally a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are packaged in dosages that match a chrono-dosing regimen comprising:

Week 1:
20 mg propranolol, 75 mg etodolac in the AM
20 mg propranolol at 3 PM
300 mg etodolac in the PM
Week 2—option 1
35 mg propranolol, 75 mg etodolac, 400 mg sorafenib in the AM
25 mg propranolol at 3 PM
600 mg etodolac in the PM
Week 2—option 2
35 mg propranolol, 75 mg etodolac, 400 mg sorafenib in the AM
25 mg propranolol at 3 PM
600 mg etodolac, 400 mg sorafenib in the PM
Week 3 same as Week 2
Week 4
35 mg propranolol,
25 mg propranolol at 3 PM In alternative embodiments, this "4 week cycle" continues until disease progression or intolerance to sorafenib at which time sorafenib can be discontinued. If patients cannot tolerate the higher propranolol or etodolac at week 2 they can go back to the Week 1 dose.

In alternative embodiments, the first cycle is dose escalation and adjustment; and after that the cycle is 4 weeks with 3 weeks on drug and 1 week off etodolac. In alternative embodiments, for patients with advanced cancer who are likely to live less than 18 months, the week 4 removal of etodolac would not be done—that is, once they get through the dose adjustments they would stay on all drugs.

In alternative embodiments, the therapeutic drug combination is formulated for administration once a day, b.i.d. or t.i.d, or weekly, or biweekly, or monthly. In alternative embodiments, the beta adrenergic receptor antagonist (a beta blocker) or propranolol or equivalent; the non-steroidal anti-inflammatory drug or NSAID or etodolac or equivalent; and also optionally a 4-[4-[[4-chloro-3-(trifluoromethyl) phenyl]carbamoylamino]phenoxy]-N-methyl-pyridine-2-carboxamide or a bioisostere thereof, or a sorafenib or NEXAVAR™ or any equivalent thereof, are formulated for administration once a day, b.i.d. or t.i.d, or weekly, or biweekly, or monthly.

In alternative embodiments, the therapeutic combination of drugs are formulated for administration intravenously, topically, orally, by inhalation, by infusion, by injection, by inhalation, intraperitoneally, intramuscularly, subcutaneously, intra-aurally, for intra-articular administration, for intra-mammary administration, for topical administration or for absorption through epithelial or mucocutaneous linings.

In alternative embodiments, provided are: a device, a medical device, an implant, a breast implant, a prosthesis, a stent, a catheter, comprising a therapeutic combination of therapeutic agents or drugs as provided herein.

In alternative embodiments, provided are: a pharmaceutical composition or formulation comprising the therapeutic combination as provided herein; and the pharmaceutical composition or formulation can further comprise a pharmaceutically acceptable excipient. In alternative embodiments, the pharmaceutical composition or formulation is formulated or manufactured as a feed, a food, a food or feed concentrate, a pellet, a lozenge, a liquid, a lotion, an implant, a nanoparticle, an elixir, an aerosol, a spray, an aerosol, an inhalant, a powder, a tablet, a pill, a capsule, a gel, a geltab, a nanosuspension, a nanoparticle, a patch, a microgel or a suppository.

In alternative embodiments, provided are method and uses for treating, preventing or ameliorating a tumor or a cancer, comprising: applying or administering to an individual in need thereof; or, applying or administering to an effected tissue: the therapeutic combination as provided herein, or a pharmaceutical composition or formulation as provided herein, wherein optionally the therapeutic agents or drugs are administered separately or together, or at the same time, or in synchrony, or by chrono-dosing, or one of the therapeutic agents or drugs is administered before another of the therapeutic agents or drugs, and optionally the therapeutic agents or drugs are formulated for administration intravenously (IV), parenterally, nasally, topically or locally, orally, or by liposome, implant or vessel-targeted nanoparticle delivery.

In alternative embodiments of the methods and uses, the cancer or tumor is: a hepatocarcinoma, a hepatocellular carcinoma (HCC), an adenocarcinoma, a metastatic adenocarcinoma of the liver, or an advanced hepatocellular carcinoma, a pancreatic cancer, an adenocarcinoma, a mastocytoma or a mast cell tumor, an ovarian cancer, a non-small cell lung cancer, small cell lung cancer, melanoma, retinoblastoma, breast tumor, colorectal carcinoma, leukemia, lymphoma, acute lymphoblastic leukemia (ALL) or acute lymphoid leukemia, acute myeloid leukemia (AML), a histiocytic sarcoma, a brain tumor, an astrocytoma, a glioblastoma, a neuroma, a neuroblastoma, a colon carcinoma, cervical carcinoma, sarcoma, prostate tumor, bladder tumor, tumor of the reticuloendothelial tissues, Wilm's tumor, ovarian carcinoma, a bone cancer, an osteosarcoma, a renal cancer, or head and neck cancer, oral cancer, a laryngeal cancer, or an oropharyngeal cancer.

In alternative embodiments, provided are methods for treating, preventing or ameliorating a tumor or a cancer, comprising:

(a) applying or administering to an individual in need thereof or, applying or administering to an effected tissue; the therapeutic combination as provided herein, or a pharmaceutical composition or formulation as provided herein, wherein optionally the therapeutic agents or drugs are administered separately or together, or at the same time, or in synchrony, or by chrono-dosing, or one of the therapeutic agents or drugs is administered before another of the therapeutic agents or drugs, and optionally the therapeutic agents or drugs are formulated for administration intravenously (IV), parenterally, nasally, topically or locally, orally, or by liposome, implant or vessel-targeted nanoparticle delivery; and (b) administering to the individual in need thereof:
  (i) a systemic anti-cancer or anti-tumor treatment, wherein optionally the systemic anti-cancer or anti-tumor treatment comprises administration of a drug, a biologic, a nutrient, an anti-cancer or anti-tumor dietary regimen, a radioactive agent, a tumor ablative agent, or (ii) an anti-cancer or anti-tumor radiotherapy or a proton beam therapy, wherein the therapeutic combination or pharmaceutical composition or formulation of (a) is administered before the anti-cancer or anti-tumor treatment of (b), or both are administered consecutively, or the therapeutic combination or pharmaceutical composition or formulation of (a) is administered after the anti-cancer or anti-tumor treatment of (b), or any combination thereof.

In alternative embodiments, the method and uses can further comprise (or comprise use of): an anti-cancer or anti-tumor radiotherapy or a proton beam therapy.

In alternative embodiments, provided are Uses of the therapeutic combination as provided herein in the manufacture of a medicament. In alternative embodiments, provided are Uses of the therapeutic combination as provided herein in the manufacture of a medicament for treating a cancer or a tumor. In alternative embodiments of the uses and methods, the cancer or tumor is: a hepatocarcinoma, a hepatocellular carcinoma (HCC), an adenocarcinoma, a metastatic adenocarcinoma of the liver, or an advanced hepatocellular carcinoma, a pancreatic cancer, an adenocarcinoma, a mastocytoma or a mast cell tumor, an ovarian cancer, a non-small cell lung cancer, small cell lung cancer, melanoma, retinoblastoma, breast tumor, colorectal carcinoma, leukemia, lymphoma, acute lymphoblastic leukemia (ALL) or acute lymphoid leukemia, acute myeloid leukemia (AML), a Histiocytic sarcoma, a brain tumor, an astrocytoma, a glioblastoma, a neuroma, a neuroblastoma, a colon carcinoma, cervical carcinoma, sarcoma, prostate tumor, bladder tumor, tumor of the reticuloendothelial tissues, Wilm's tumor, ovarian carcinoma, a bone cancer, an osteosarcoma, a renal cancer, or head and neck cancer, oral cancer, a laryngeal cancer, or an oropharyngeal cancer.

In alternative embodiments or methods and uses as provided herein, a therapeutic combination of a beta blocker (e.g., a propranolol) and an NSAID (e.g., an etodolac) (e.g., VT-122) is given to an individual in need thereof one day to two weeks, or about one week, before beginning the therapeutic combination of a beta blocker (e.g., a propranolol) and an NSAID (e.g., an etodolac) and a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, and optionally the therapeutic combination of a beta blocker (e.g., a propranolol) and an NSAID (e.g., an etodolac) and a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, is given for between one and three weeks, followed by no treatment (no administration of a therapeutic combination) for one day to ten days, e.g., one week, and then begin the therapeutic combination treatment again, optionally for one, two, three, four or more cycles, and optionally including the one week of the beta blocker (e.g., a propranolol) and an NSAID (e.g., an etodolac) (e.g., VT-122) alone.

The details of one or more aspects of the invention are set forth in the description below. Other features, objects, and advantages of the invention will be apparent from the description and from the claims.

All publications, patents and patent applications cited herein are hereby expressly incorporated by reference for all purposes.

DESCRIPTION OF DRAWINGS

The drawings set forth herein are illustrative of embodiments described herein and are not meant to limit the scope of the invention as encompassed by the claims.

FIG. 3 schematically illustrates a Table 1 showing the potential benefits of COX-2 and adrenergic inhibition in the oncology setting.

Like reference symbols in the various drawings indicate like elements.

DETAILED DESCRIPTION

Figure 1:
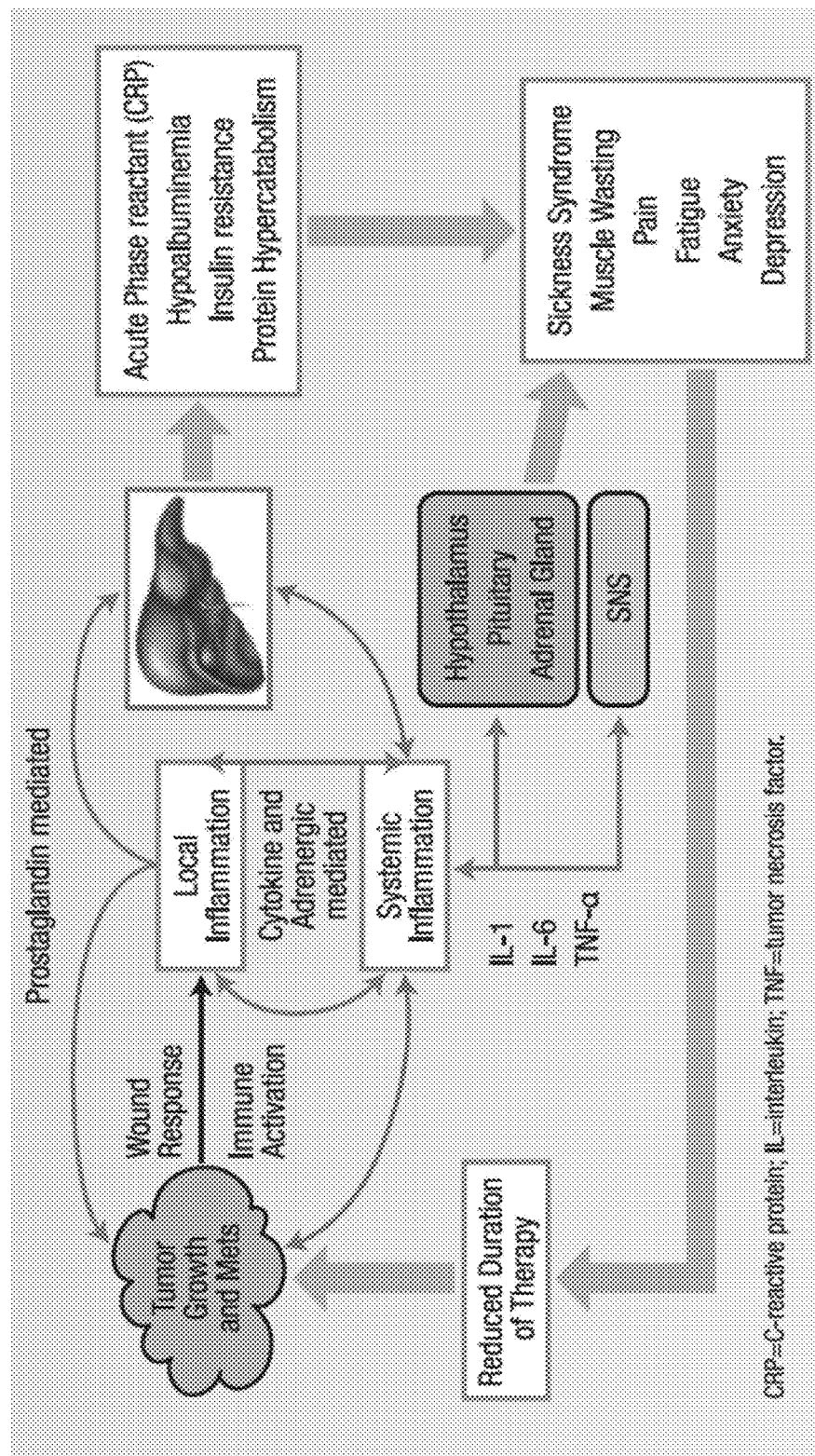
FIG. 1 schematically illustrates a model of onco-inflammation, cancer and sickness syndrome, showing adrenergic and prostaglandin regulation.

In alternative embodiments, provided are therapeutic combinations, pharmaceutical compositions, formulations, kits and devices for treating, preventing or ameliorating a tumor or a cancer, and methods for treating, preventing or ameliorating a tumor or a cancer. In alternative embodiments, provided are therapeutic combinations, pharmaceutical compositions, formulations, kits and devices comprising: a beta adrenergic receptor antagonist (a "beta blocker"); a non-steroidal anti-inflammatory drug (a NSAID); a 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof. In alternative embodiments, the therapeutic combinations further comprise an anti-cancer or anti-tumor antibody, a cytokine, and/or a chemotherapeutic agent.

In alternative embodiments, the tumor or cancer treated is a hepatocellular carcinoma, a hepatocellular carcinoma (HCC), an adenocarcinoma, a metastatic adenocarcinoma of the liver, or an advanced hepatocellular carcinoma, an adenocarcinoma, a metastatic adenocarcinoma of the liver, or an advanced hepatocellular carcinoma. Although for hepatocellular carcinoma treatments administration of sorafenib or NEXAVAR™ has increased median overall survival (OS) clearly other therapies and treatment modalities are needed to improve survival in this patient population, and exemplary therapeutic combinations of this invention do address this issue and solve this problem, as demonstrated by studies described in Example 1 and Example 2, below.

In alternative embodiments the cancer is a dysfunctional cell condition. In alternative embodiments the cancer or dysfunctional cell condition comprises (is) any metastatic or benign tumor, and the methods or uses as provided herein are used for ameliorating, treating (killing, eliminating, stopping the growth and/or metastasis of) cancer stem cells or cancer cells from: a hepatocellular carcinoma (HCC), a metastatic adenocarcinoma of the liver, advanced hepatocellular carcinoma, a pancreatic cancer, an adenocarcinoma, a metastatic adenocarcinoma of the pancreas (mPCa), lung cancer, bone cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, a neoplasm of the central nervous system (CNS), primary CNS lymphoma, spinal axis tumors, brain stem glioma or pituitary adenoma, and any combination thereof.

While the invention is not limited by any particular mechanism of action, preclinical studies have shown that propranolol, a beta blocker developed for cardiovascular conditions and now also has obtained labeled indications including treatment of unintentional tremor, migraine headaches, anxiety and infant hemangioma, and etodolac a COX-2 selective nonsteroidal anti-inflammatory developed for pain management of osteoarthritis (it is associated with a very low incidence of gastrointestinal side effects and has a COX-2 selectivity similar to that of celecoxib), effectively block adrenergic and prostaglandin signaling pathways, respectively, can dampen tumor promoting inflammation and switch immune states.

Additionally, while the invention is not limited by any particular mechanism of action, the discovery provided herein that propranolol and etodolac can synergize with sorafenib in the treatment of cancer, e.g., a hepatocellular carcinoma, a hepatocellular carcinoma (HCC), an adenocarcinoma, a metastatic adenocarcinoma of the liver, or an advanced hepatocellular carcinoma, has a basis in the modes of action of propranolol and etodolac (e.g., VT-122), for example, propranolol and etodolac have defined modes of action on known signaling pathways through G-protein couples receptors (GPCRs). FIG. 1 schematically illustrates a model of onco-inflammation, cancer and sickness syndrome, showing adrenergic and prostaglandin regulation.

Regulation of indoleamine 2,3-dioxygenase (IDO) and hypoxia inducing factor (HIF)-1 alpha have been shown to be regulated through adrenergic and prostaglandin signaling pathways.

Figure 2:
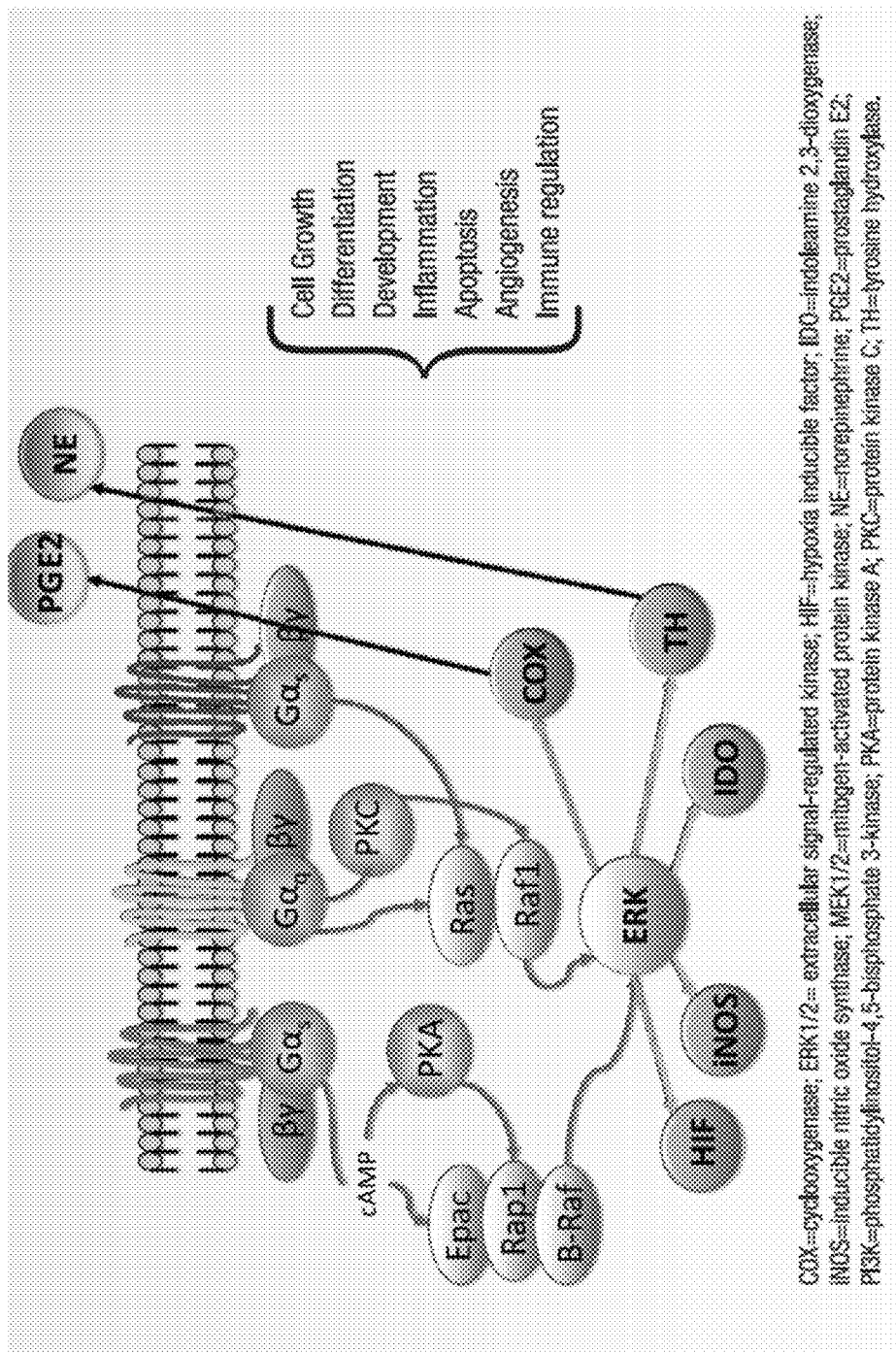
FIG. 2 schematically illustrates the relationship of adrenergic and prostaglandin signaling pathways.

While the invention is not limited by any particular mechanism of action, regulation of inducible nitric oxide synthase (iNOS), COX-2, tyrosine hydroxylase (TH) all play roles in cancer development, and the signaling pathways for GPCRs are highly redundant with pathways for tyrosine kinases inhibitors, and by inhibiting GPCRs on more cell types additional clinical benefits are realized, as schematically illustrated in FIG. 2, illustrating the relationship of adrenergic and prostaglandin signaling pathways. The potential benefits of COX-2 and adrenergic inhibition in the oncology setting are illustrated in Table 1, which is illustrated in FIG. 3.

While the invention is not limited by any particular mechanism of action, VT-122 (Vicus Therapeutics, Morristown N.J.), comprising both propranolol and etodolac, inhibits adrenergic beta receptors 1-2, COX-2 & TRPA1 and the MAPK, PI3K, PKA, STAT3 & nociception signaling cascades.

While the invention is not limited by any particular mechanism of action, by chrono-modulating multiple signaling cascades in the tumor microenvironment and the tumor-induced systemic environment, VT-122:

Damps tumor promoting inflammation: inhibits perineural invasion, metastasis, angiogenesis, lymphangiogenesis, fibrogenesis and gluconeogenesis.

Restores immune surveillance: reduces myeloid derived suppressor cells (MDSCs), activates NK cells and switches tumor-associated macrophages (TAMs) and T-cells from M2/Th2 to M1/Th1 state Improves treatment tolerance: reduces inflammation potentiated hand-foot-syndrome, chemotherapy-induced-peripheral-neuropathy and cachexia.

While the invention is not limited by any particular mechanism of action, VT-122 is differentiated from other immunotherapies along several dimensions because administration of VT-122 can:

Target multiple un-drugged pathways within the tumor microenvironment and tumor-induced systemic environment.

Modulate both the innate and adaptive immune systems.

Reduce side-effects of sorafenib in liver cancer and GemNab in pancreatic cancer.

Enable patient adherence to the right drugs at the right doses and at the right times with a unique controlled release formulation and blister card packaging system.

While the invention is not limited by any particular mechanism of action, propranolol and etodolac target the two major stress systems that are activated in cancer, surgery and chemotherapy:

Induce changes in tumor microenvironment, immune system, liver and HPA,

Lead to tumor promotion and immune tolerance.

While the invention is not limited by any particular mechanism of action, propranolol and etodolac induce multiple pathways within the MAP Kinase signaling pathway that result in:

Macrophage M2/M1 and NK Cytotoxic innate immune switch,

T-cell Th2/Th1 adaptive immune switch,

Inhibition of Indoleamine 2,3-dioxygenase,

Inhibition of HIF-1 alpha and angiogenesis,

Inhibition of hepatocyte gluconeogenesis/hypercatabolism.

In alternative embodiments provided are products of manufacture comprising a blister package, a lidded blister or a blister card or packet, a clamshell, a tray or a shrink wrap comprising a therapeutic combination as provided herein, or the pharmaceutical composition or formulation as provided herein. In alternative embodiments the products of manufacture can comprise a blister package, a lidded blister or a blister card or packet, a clamshell, a tray or a shrink wrap comprising a therapeutic combination as provided herein, or the pharmaceutical composition or formulation as provided herein, wherein the therapeutic combination or pharmaceutical composition or formulation are manufactured and/or formulated for at least two, three, four or five or more dosage administrations; or the therapeutic combination or pharmaceutical composition or formulation are manufactured and/or formulated for once a day, or b.i.d. (twice a day), or t.i.d. (three times a day), or four times a day, administration.

In alternative embodiments, a drug combination as provided herein is formulated, packaged or designed for drug regimen compliance of a cancer patient population, a pediatric or geriatric population, or a mentally compromised patient population.

In alternative embodiments drug combination(s) as provided herein are formulated, packaged or designed for drug regimen compliance of a cancer patient population having mild or severe mental retardation, slow cognition, dementia, senility, Alzheimer's disease, traumatic brain injury, chemical brain damage, mental diseases (e.g., dissociative disorder, obsessive-compulsive disorder, delusional disorder, schizophrenia, mania, panic disorder, depression, dyslexia, any learning disability and the like) post-traumatic stress disorder, traumatic war neurosis, post-traumatic stress syndrome (PTSS), physical disability (e.g., blindness).

In alternative embodiments of the products of manufacture as provided herein the therapeutic combination or pharmaceutical composition or formulation are formulated (e.g., manufactured) as one dosage administration in the morning and one dosage administration in the evening; or are formulated as one dosage administration in the morning, one dosage mid-day and one dosage administration in the evening. In one aspect, the dosage schedule provides a relatively higher dose of one drug in the morning (the AM) than in the evening, and a relatively higher dose of another medication in the evening than in the morning. For example, in alternative embodiments the therapeutic combination or the pharmaceutical composition are formulated for multiple administrations, e.g., at least two administrations, one in the morning and one in the evening, wherein the dosage schedule provides a relatively higher dose of beta blocker in the morning (the AM) than in the evening, and a relatively higher dose of an anti-inflammatory medication in the evening than in the morning.

In alternative embodiments, the products of manufacture or formulations as provided herein comprise a therapeutic combination as provided herein or the pharmaceutical composition or formulation as provided herein, and a nutritional supplement, or food supplement or feed supplement.

Methods of Administration

In alternative embodiments, provided herein are therapeutic combinations of drugs, pharmaceutical compositions, preparations and kits, that can be administered by several routes, for formulated for administration by any of several routes, including intravenous, topical and oral, subcutaneous, mucosal, aerosol, or combinations thereof. In exemplary alternative embodiments, the therapeutic combination of drugs are formulated for administration intravenously, topically, orally, by inhalation, by infusion, by injection, by inhalation, intraperitoneally, intramuscularly, subcutaneously, intra-aurally, for intra-articular administration, for intra-mammary administration, for topical administration or for absorption through epithelial or mucocutaneous linings.

The invention provides a device, a medical device, an implant, a breast implant, a prosthesis, a stent, a catheter, comprising a therapeutic combination of therapeutic agents or drugs of the invention.

For example, one embodiment comprises a product of manufacture comprising a pharmaceutical composition or a formulation, a blister package, a lidded blister or a blister card or packet, a clamshell, a tray or a shrink wrap, or a kit, comprising: therapeutic combinations of drugs, pharmaceutical compositions or preparations as provided herein.

In alternative embodiments, although all ingredients can be in one blister package, a lidded blister or a blister card or packet, a clamshell, a tray or a shrink wrap, or a kit, separate ingredients can be formulated e.g., for topical application, for oral or for topical application. Each ingredient can be either separately packaged, or can be formulated as one unit dose, e.g., as one tube (e.g., with gel, lotion etc.), ampoule, blister packette and the like.

In alternative embodiments, provided herein are forms of compositions, preparations and kits that can be administered by inhalation, infusion or injection, (e.g., intraperitoneal, intramuscular, subcutaneous, intra-aural, intra-articular, intra-mammary, etc.), topical application (e.g., on areas, such as eyes, ears, skin or on afflictions such as wounds, burns, etc.), and by absorption through epithelial or mucocutaneous linings (e.g. vaginal and other epithelial linings, gastrointestinal mucosa, etc.). Methods are known for making compositions, preparations and kits containing the present components that are suitable for each of these methods of administration as well as other methods of administration that are known in the art.

In alternative embodiments, provided herein are compositions, preparations and kits in liquid forms that can be administered orally. The compositions, preparations and kits can be also prepared as capsules, gels, geltabs, tablets, powders, sprays, aerosols, pellets (e.g. for animal consumption), suppositories, lotions, patches or adhesives (e.g., for the skin), or creams and ointments. The compositions, preparations and kits can be also prepared as physiological solutions suitable for I.V. administration or other parenteral administration.

In one aspect, a multi-ingredient kit as provided herein comprises (contains) two or more ingredients. An amount may be determined, e.g. by mass or by weight or by molar amount. In another aspect, a multi-ingredient kit may contain two or more ingredients in unequal amounts. In another aspect, a multi-ingredient kit may contain two or more ingredients in approximately equal amounts and/or one or more ingredients that are not in unequal amounts.

In another embodiment, said multi-ingredient kit may contain two or more ingredients that are admixed. In another aspect, said multi-ingredient kit may contain two or more ingredients that are not admixed. In another aspect, said multi-ingredient kit may contain two or more ingredients that are partially admixed. In another aspect, said multi-ingredient kit may contain two or more ingredients that are at least partially admixed, as well as one or more ingredients that are not admixed. An ingredient in a multi-ingredient kit may be liquid forms that can be administered orally.

Dosaging

In alternative embodiments of the therapeutic combination, the 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are administered using standard dosage and administration; for example, dosaging and administration regimen as on the FDA approved label (the FDA has approved nab-paclitaxel (NEXAVAR™) as a first-line treatment for patients with hepatic adenocarcinoma.

In alternative embodiments of the therapeutic combination, the drug combination is packaged in dosages that match a chrono-dosing regimen to match an optimal dose for the time of day. For example, in exemplary alternative embodiments, the beta adrenergic receptor antagonist or a beta blocker or equivalent, or a propranolol or equivalent; the non-steroidal anti-inflammatory drug or NSAID or equivalent, or etodolac or equivalent; and/or the 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are packaged in dosages that match a chrono-dosing regimen to match an optimal dose for the time of day.

In exemplary alternative embodiments, the beta adrenergic receptor antagonist or beta blocker or equivalent or propranolol or equivalent; the non-steroidal anti-inflammatory drug or NSAID or equivalent or etodolac or equivalent; and/or the 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are packaged in dosages that match a chrono-dosing regimen comprising:

(a) in the AM, 20 mg beta adrenergic receptor antagonist (a beta blocker), e.g., a propranolol or equivalent, 200 mg NSAID, e.g., an etodolac or equivalent; in the afternoon, 10 mg beta blocker, 200 mg NSAID, e.g., an etodolac or equivalent; in the PM, 10 mg beta blocker, 400 mg NSAID;

(b) in the AM 40 mg beta adrenergic receptor antagonist (a beta blocker), e.g., a propranolol or equivalent, 200 mg NSAID, e.g., an etodolac or equivalent; in the afternoon 20 mg beta blocker, 200 mg NSAID; in the evening, 20 mg propranolol, 400 mg NSAID;

(c) in the AM 80 mg beta adrenergic receptor antagonist (a beta blocker), e.g., a propranolol or equivalent, 200 mg NSAID; in the afternoon 40 mg beta blocker, 200 mg NSAID, in the evening 40 mg, NSAID; or (d) a dose escalation comprising a regimen of (a) to (b) to (c).

In exemplary alternative embodiments, the beta adrenergic receptor antagonist or beta blocker or equivalent or propranolol or equivalent; the non-steroidal anti-inflammatory drug or NSAID or equivalent or etodolac or equivalent; and/or the 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are packaged in dosages that match a chrono-dosing regimen comprising:

Start: AM, 20 mg propranolol, 200 mg etodolac; afternoon, 10 mg propranolol, 200 mg etodolac; PM 5 mg propranolol, 400 mg etodolac;

Dose Escalation 1: AM 40 mg propranolol, 200 mg etodolac; afternoon 20 mg propranolol, 200 mg etodolac; evening, 10 mg propranolol, 400 mg etodolac;

Dose escalation 2: AM 80 mg propranolol, 200 mg etodolac; afternoon 40 mg propranolol, 200 mg etodolac, evening 20 mg, etodolac.

In exemplary alternative embodiments, the therapeutic drug combination is formulated for administration once a day, b.i.d. or t.i.d, or weekly, or biweekly, or monthly. In exemplary alternative embodiments, the beta adrenergic receptor antagonist (a beta blocker) or propranolol or equivalent; the non-steroidal anti-inflammatory drug or NSAID or etodolac or equivalent; and/or the 4-[4-[[4-chloro-3-(trifluoromethyl)phenyl]carbamoylamino]phenoxy]-N-methyl-pyridine-2-carboxamide or a bioisostere thereof, or a sorafenib or NEXAVAR™ or any equivalent thereof, are formulated for administration once a day, b.i.d. or t.i.d, or weekly, or biweekly, or monthly.

Packaging

In alternative embodiments, provided are therapeutic combinations, preparations, formulations and/or kits, comprising combinations of ingredients, as described herein. In one aspect, each member of the combination of ingredients is manufactured in a separate package, kit or container; or, all or a subset of the combinations of ingredients are manufactured in a separate package or container. In alternative aspects, the package, kit or container comprises a blister package, a clamshell, a tray, a shrink wrap and the like.

In one aspect, the package, kit or container comprises a "blister package" (also called a blister pack, or bubble pack). In one aspect, the blister package is made up of two separate elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, provided are blister packs, clamshells or trays comprising a composition (e.g., a (the multi-ingredient combination of drugs as provided herein) combination of active ingredients) as provided herein. Blister packs, clamshells or trays can be designed to be non-reclosable, so consumers can tell if a package has already opened. They are used to package for sale goods where product tampering is a consideration, such as the pharmaceuticals as provided herein. In one aspect, a blister pack as provided herein comprises a molded PVC base, with raised areas (the "blisters") to contain the tablets, pills, etc. comprising the combinations as provided herein, covered by a foil laminate. Tablets, pills, etc. are removed from the pack either by peeling the foil back or by pushing the blister to force the tablet to break the foil. In one aspect, a specialized form of a blister pack is a strip pack. In one aspect, in the United Kingdom, blister packs adhere to British Standard 8404.

In one aspect, a blister packs also comprise a method of packaging where the compositions comprising combinations of ingredients as provided herein are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. as provided herein are used, and they can comprise of two vacuum-formed PVC sheets meshed together at the edges, with the informative card inside. These can be hard to open by hand, so a pair of scissors or a sharp knife may be required to open.

In one aspect, blister packaging comprises at least two components (e.g., is a multi-ingredient combination of drugs as provided herein): a thermoformed "blister" which houses the product (e.g., a pharmaceutical combination as provided herein), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or as large as you would like, but there are limitations and cost considerations in going to an oversized blister card. Conventional blister packs can also be sealed (e.g., using an AERGO 8 DUO™, SCA Consumer Packaging, Inc., DeKalb Ill.) using regular heat seal tooling. This alternative aspect, using heat seal tooling, can seal common types of thermoformed packaging.

Blister Packaging

In alternative embodiments, provided are therapeutic combinations, preparations, formulations and/or kits can be manufactured as "blister packages" or as a plurality of packettes, including as lidded blister packages, lidded blister or blister card or packets or packettes, or a shrink wrap.

In alternative embodiments, laminated aluminum foil blister packs are used, e.g., for the preparation of drugs designed to dissolve immediately in the mouth of a patient. This exemplary process comprises having the drug combinations as provided herein prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminum (e.g., alufoil) lidding material. In one aspect, hermetically-sealed high barrier aluminum (e.g., alufoil) laminates are used. In one aspect, any products of manufacture as provided herein, including kits or blister packs, use foil laminations and strip packs, stick packs, sachets and pouches, peelable and non-peelable laminations combining foil, paper, and film for high barrier packaging.

In alternative embodiments, any products of manufacture as provided herein, including kits or blister packs, include memory aids to help remind patients when and how to take the drug. This safeguards the drug's efficacy by protecting each pill until it's taken; gives the product or kit portability, makes it easy to take a dose anytime or anywhere. In alternative embodiments, each subcompartment is color coded, or coded for digital recognition, e.g., braille coded, or all compartments to be taken at the same time are coded in the same format (e.g., color).

Bioisosteres, Stereoisomers, Racemers

In alternative embodiments, the invention also provides bioisosteres of compounds used to practice embodiments as provided herein, e.g., a 4-[4-[[4-chloro-3-(trifluoromethyl) phenyl]carbamoylamino]phenoxy]-N-methyl-pyridine-2-carboxamide. In alternative embodiments, bioisosteres used to practice embodiments as provided herein are compounds comprising one or more substituent and/or group replacements with a substituent and/or group having substantially similar physical or chemical properties which produce substantially similar biological properties to a compound used to practice embodiments as provided herein, or stereoisomer, racemer or isomer thereof. In one embodiment, the purpose of exchanging one bioisostere for another is to enhance the desired biological or physical properties of a compound without making significant changes in chemical structures.

For example, in one embodiment, bioisosteres of compounds used to practice embodiments as provided herein are made by replacing one or more hydrogen atom(s) with one or more fluorine atom(s), e.g., at a site of metabolic oxidation; this may prevent metabolism (catabolism) from taking place. Because the fluorine atom is similar in size to the hydrogen atom the overall topology of the molecule is not significantly affected, leaving the desired biological activity unaffected. However, with a blocked pathway for metabolism, the molecule may have a longer half-life or be less toxic, and the like.

The invention will be further described with reference to the following examples; however, it is to be understood that the invention is not limited to such examples.

EXAMPLES

Example 1: Treatment of Hepatocellular Carcinoma (HCC) by Administration of an Exemplary Combination Therapy In alternative embodiments, provided are therapeutic combinations, pharmaceutical compositions, formulations, kits and devices for treating, preventing or ameliorating a tumor or a cancer, and methods for treating, preventing or ameliorating a tumor or a cancer, wherein in one embodiment the cancer is a hepatocarcinoma, a hepatocellular carcinoma (HCC), a metastatic adenocarcinoma of the liver, an advanced hepatocellular carcinoma. This example describes data demonstrating the efficacy of an exemplary therapeutic combination as described herein.

This exemplary study was designed to evaluate the safety, tolerability and efficacy of exemplary therapeutic combinations of the invention comprising propranolol and etodolac, formulated as VT-122 for this study, and sorafenib or NEXAVAR™, in the treatment of patients with locally advanced and metastatic pancreatic cancer.

A Phase II study of propranolol and etodolac formulated as VT-122 with sorafenib compared sorafenib alone (N=24) with sorafenib and VT-122; the sorafenib and VT-122 arm resulted in: increased survival, 21 months versus 10 months (HR=0.14, P<0.001); increased 12 month survival (83.3%, or 8 out of 12); stabilization of weight; a lower prevalence of hand-foot skin reaction; and, reduced markers of inflammation.

The objection of the study described in this example was to evaluate the safety, tolerability, and efficacy of the co-administration of propranolol and etodolac formulated as VT-122 in advanced HCC patients receiving sorafenib as a standard of care first-line therapy.

Materials and Methods

Patient Selection:

Patients were adults 18 to 65 years of age with advanced HCC and a life expectancy of greater than 12 weeks who had received and tolerated sorafenib for about or greater that four weeks. Inclusion criteria were: Karnofsky performance status of equal to or greater than 50; an Eastern Cooperative Oncology Group Progressive (ECOG) score of 0 to 2; a Child-Pugh class A or B7; ability to swallow pills and take food or nutritional support orally; acceptable laboratory parameters, including platelet count of equal to or greater than 50×109/L, serum creatinine (SCr) clearance of greater than 60 mL/min or SCr of equal to or less than 1.5× the upper limit of normal, a serum albumin of less than or equal to 3.5 b/dL and/or serum CRP of equal to or greater than 3 mg/L. Selected exclusion criteria were: history of another primary cancer, with the exception of curatively resected non-melanoma skin cancer, curatively treated cervical carcinoma in situ, or other primary solid tumor with no known active disease present that in the opinion of the investigator would not affect patient outcome; current beta blocker use for portal hypertension or arrhythmia (patients on beta blockers for hypertension were allowed to change to a different anti-hypertensive class greater than or equal to one week before randomization); body mass index of greater than 17.5 kg/m$^2$; history of or current heart failure (NYHA class or greater), active coronary artery disease, unstable angina, cardiac arrhythmias requiring treatment, 2° or 3° atrioventricular block, or uncontrolled hypertension; recent (less than six months) myocardial infarction or coronary revascularization; hypotension at the time of screening (SBP of less than 100 mmHg, DBP of less than 60 mm Hg); resting heart rate of less than 60 beats per minute (bpm) at screening; recent diagnosis of bleeding varices that had not been resolved for less than 4 weeks; current chronotrope use, e.g., use of acetylcholine, digoxin, diltiazem, verapamil, atropine, dopamine, dobutamine, epinephrine, isoproterenol.

Study Design and Assessments:

This was a multi-center, randomized, double-blind, double-dummy, placebo-controlled study. Patients were randomly assigned (1:1) to received VT-122 or placebo on a background of stable-dose sorafenib.

Dosing:

Sorafenib: dose adjustments, cessation, and re-initiation as standard of care for sorafenib was permitted during the 30 days prior to randomization; randomization occurred when, in the opinion of the investigator, the patient was on a stable dose.

VT-122 (Vicus Therapeutics, Morristown N.J.): patients entered a three week dose escalation period, with propranolol maximum at 120 mg, and etodolac maximum at 600 mg. VT-122 was administered in split doses in the morning and evening.

Duration of Therapy:

After the three week dose escalation period, patients were to continue therapy for four four-week cycles.

Study Endpoints:

Primary endpoint=failure free survival, defined as reduction in sorafenib dose to less than 400 mg every other day (200 mg per day) or discontinuing of sorafenib for any reason with no intent to reinitiate therapy.

Secondary endpoint=lean body mass, overall survival, muscle function, symptom assessment.

Results:

Summary:

A total of twenty patients were treated, n=11 in the VT-122 group; n=9 in the placebo group; as illustrated in Table 2, below, which summarizes baseline disease characteristics:

TABLE 2

Baseline Demographics and Characteristics

| Variable | Sorafenib + VT-122 (n = 11) | Sorafenib + Placebo (n = 9) |
|---|---|---|
| Mean age$^a$ | 62.1 | 58.3 |
| Sex (M/F), n | 7/4 | 7/2 |
| Race, n | | |
| Hispanic | 5 | 2 |
| African American | 3 | 4 |
| Caucasian | 3 | 3 |
| Mean BMI, kg/m$^2$ | 28 | 24.8 |
| Child-Pugh Stage (A/B7), n | 5/6 | 4/5 |
| CLIP Score$^b$ | 2 | 1.6 |
| Mean Karnofsky performance status | 83.6 | 63.6 |
| Mean bilirubin, mg/L | 0.7 | 0.7 |
| Mean serum creatinine, mg/dL | 0.7 | 0.8 |
| Mean albumin, g/L | 8.1 | 3.3 |
| Mean CRP, mg/L | 26.2 | 24.1 |

$^a$P = 0.03.
$^b$CLIP score calculated by assigning a score (0, 1, or 2) to clinical factors (Child-Pugh stage, number of tumor modules and tumor extension through liver, alpha-fetoprotein, and portal vein thrombosis. Higher scores are associated with lower median survival$^2$
BMI = body mass index; CRP = C-reactive protein.

The superscript 2 in Table 2 indicates reference to: Cancer of the Liver Italian Program Investigators (1998) Hepatology 28(3):751-755.

Survival:

Overall survival: twelve month survival was greater in VT-122 (plus sorafenib)-treated patients compared with patients treated with sorafenib alone; 5/11, or 45.5% versus 3/9, or 27.3%.

Figure 4:
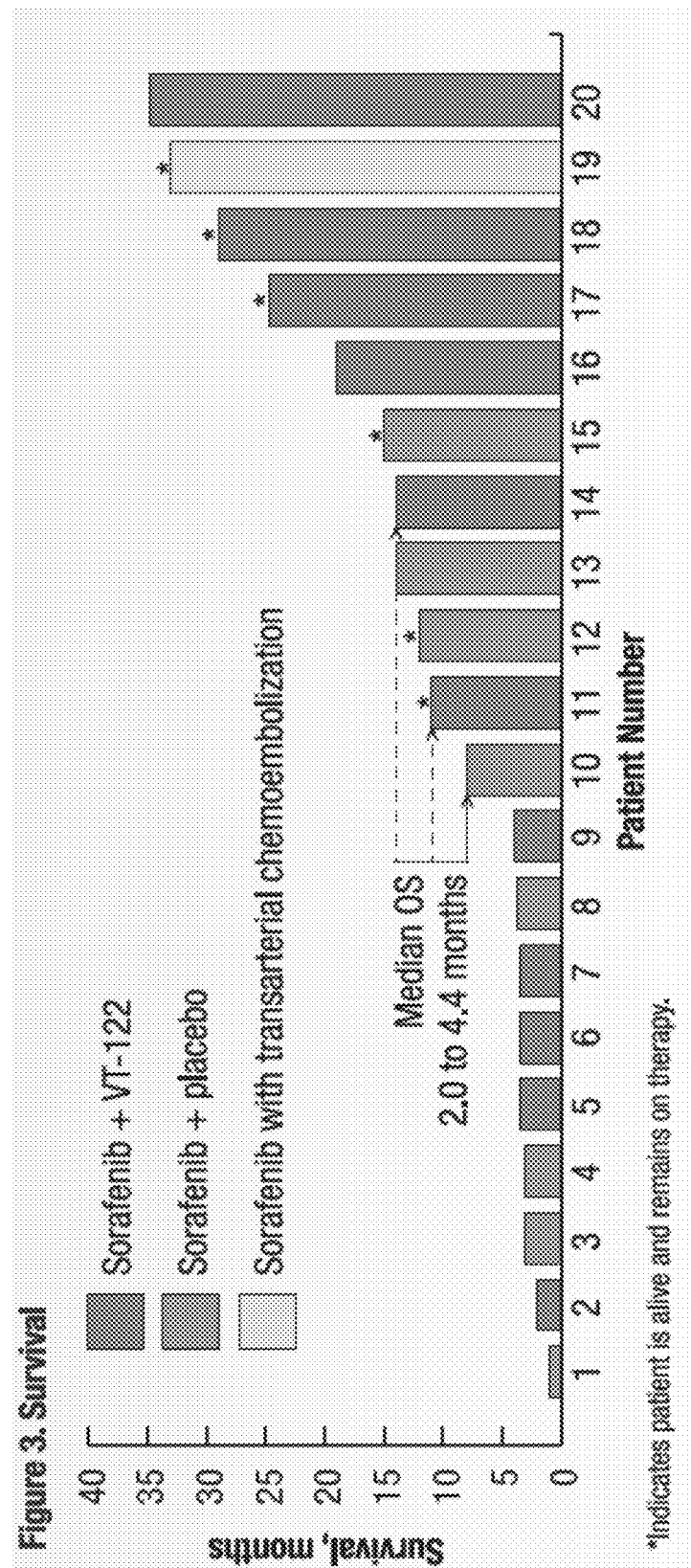
FIG. 4 graphically illustrates data from a study described in detail in Example 1, below, as summarized in Table 3, including median survival of patients in the study.

Median survival, as illustrated in Table 3, below, and as graphically illustrated in FIG. 4, was 2.0 to 4.4 months, and was greater in the VT-122 (plus sorafenib)-treated patients.

TABLE 3

Median Survival

| Variable | Sorafenib + VT-122 (n = 11) | Sorafenib + Placebo (n = 9) |
|---|---|---|
| Patients censored, n (%) | 3 (27.3) | 3 (33.3) |
| Kaplan-Meier median survival (95% CI), days | 401 (98, 1058) | 267 (32, NR) |

Safety:

No treatment-associated serious adverse events have been reported.

Figure 5:
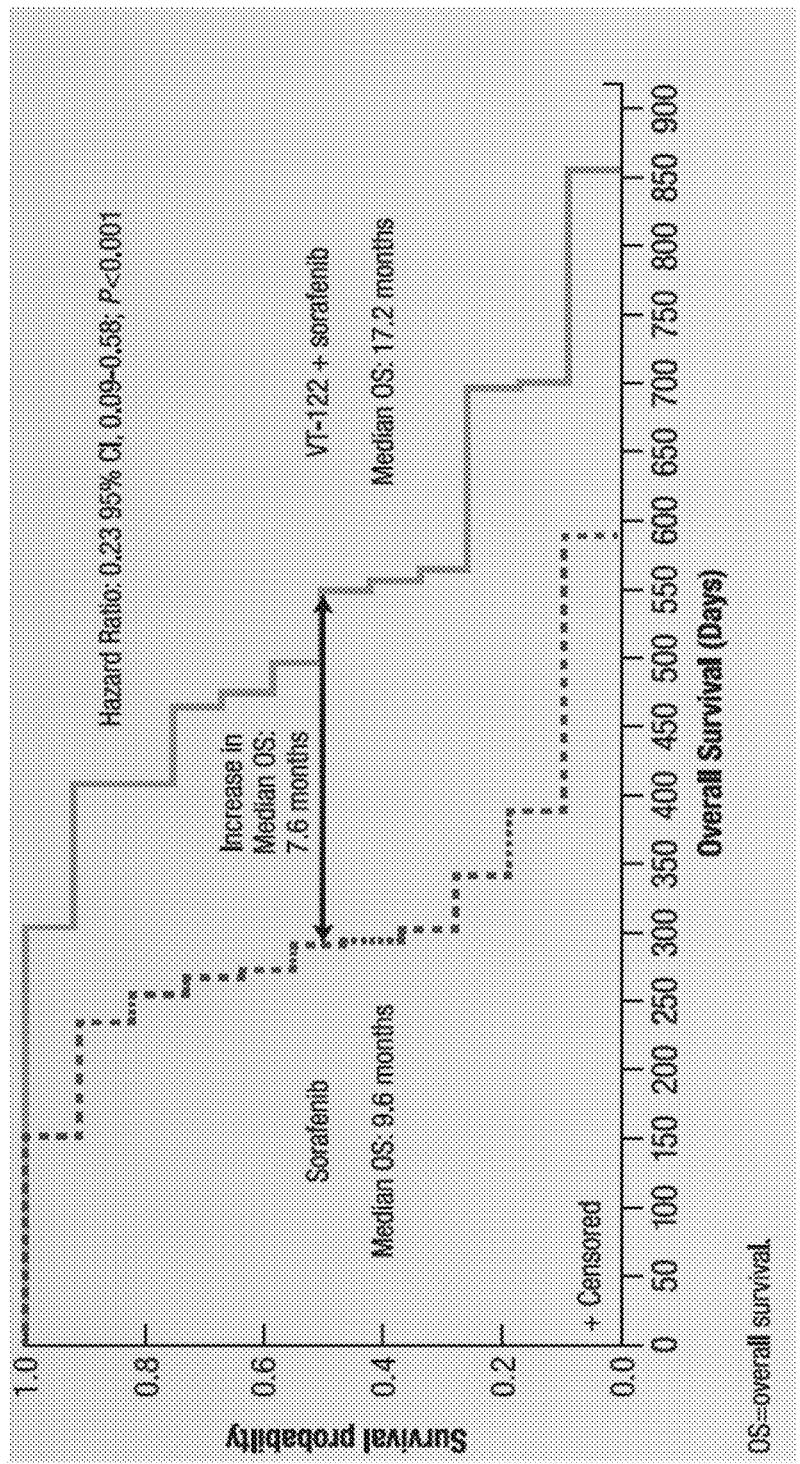
FIG. 5 graphically illustrates data from a study described in detail in Example 1, below, showing the results from a Phase II study of VT-122 showing a greater improvement in the twelve week and overall survival result.

Results from another Phase II study of VT-122 showed a greater improvement in the twelve week and overall survival result, as graphically illustrated in FIG. 5. Differences in results between the two Phase II studies may be due to differences in populations, study dosing of VT-122, for example, study design and/or VT-122 dosing:

Study Design:

in the first Phase II study, VT-122 was initiated two weeks prior to sorafenib therapy rather than after sorafenib initiation as was done in the study described in this Example; this may have caused an enhanced reduction in inflammation prior to sorafenib initiation and resulted in better outcomes;

VT-122 Dosing:

in the previous study, propranolol was administered at 8 AM at 20 mg and at 3 PM at 20 mg, and etodolac was administered at 300 mg at 8 AM and 8 PM; daytime only administration of propranolol may preserve night-time circulating melatonin levels, which induces lymphocyte IL-2 expression and block PGE-2 immune suppression (see e.g., Carrillo-Vico et al. (2003) FASEB 17(6):755-757). In the study described in this Example, administration of propranolol at 8 PM may have disrupted the melatonin cycle and adversely affected outcomes.

Conclusions:

Co-administration of VT-122 with sorafenib was well-tolerated and showed an increase in duration of therapy and overall survival (OS) versus sorafenib alone, and the studies suggested that the second chrono-dosed administration of propranolol in the afternoon versus the evening results in better OS.

Results from this Phase 2 study of VT-122 demonstrate that it is generally well-tolerated and (in the VT-122 (plus sorafenib)-treated patient group) it is associated with an increase in twelve month survival and median overall survival compared with sorafenib alone. Thus, the exemplary therapeutic combination comprising VT-122 and sorafenib or NEXAVAR™ was demonstrated to be effective in increasing overall survival (OS). The exemplary therapeutic combination comprising VT-122 did not result in serious adverse events.

Example 2: Treatment of Hepatocellular Carcinoma (HCC) by Administration of an Exemplary Combination Therapy In alternative embodiments, provided are therapeutic combinations, pharmaceutical compositions, formulations, kits and devices for treating, preventing or ameliorating a tumor or a cancer, and methods for treating, preventing or ameliorating a tumor or a cancer, wherein in one embodiment the cancer is a hepatocarcinoma, a hepatocellular carcinoma (HCC), a metastatic adenocarcinoma of the liver, an advanced hepatocellular carcinoma. This example describes data demonstrating the efficacy of an exemplary therapeutic combination as described herein, and in particular described the enhanced survival benefit from sorafenib co-administered with beta blocker and COX-2 inhibitors in patients with advanced hepatocellular carcinoma (HCC).

Aim of Study:

Preclinical and clinical reports in various solid tumors including HCC showed an improvement in relapse free survival and overall survival by the concomitant use of beta blockers and/or selective NSAIDs (COX-2 inhibitors). Data on the use of the combination in advanced hepatocellular carcinoma patients are lacking. The aim of this study was to evaluate the impact of the co-administration of the beta blocker propranolol (P) and the selective COX-2 inhibitor etodolac (E) on clinical outcome in advanced HCC patients receiving sorafenib (S) as standard of care first line therapy.

Methods:

Patients with advanced HCC were eligible for this randomized investigator initiated trial. Patients received propranolol (P) and etodolac (E) (or "PE") daily for one week prior to starting sorafenib (S). PE was administered to maximize the therapeutic benefit and minimize side effects. The primary endpoint was survival.

Twenty-four patients were randomized to either sorafenib alone (Group S) or sorafenib after one week of propranolol and etodolac (Group SPE). Population: median age, 54.6 years; 74% male; BMI, 23.0; C-reactive protein (CRP), 69.3; cirrhosis (8.8%), fibrosis (50%), hepatitis B positive (85%). The patient population is summarized:

| Factor | Sorafenib (n = 12) | Sorafenib + PE (n = 12) | P-value |
|---|---|---|---|
| Age | 54.9 | 49.9 | .011 |
| Male/Female | 10/2 | 11/1 | |
| Prior TACE/resection | 9% | 9% | |
| BMI | 22.6 | 22.8 | |
| Heart Rate | 97.6 | 93.5 | |
| HepB positive | 8/12 | 7/12 | |
| ECOG 0/1 | 25% | 75% | 0.013 |

Figure 6:
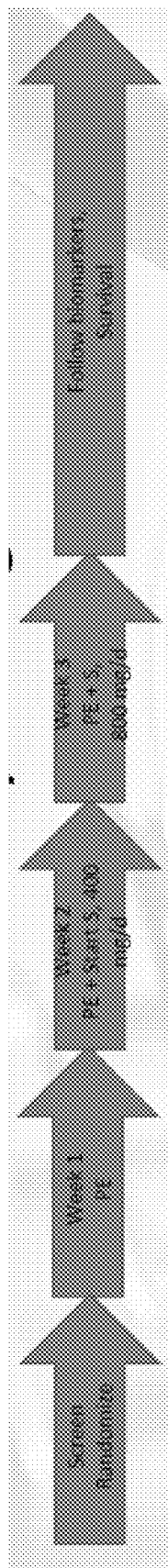
FIG. 6 schematically illustrates the study design of a clinical study described in detail in Example 1, below.

Study Design:

The study design is schematically illustrated in FIG. 6. Patients received PE daily for one week prior to starting S.
Dosing for PE was as follows:
8 AM 20 mg propranolol+300 mg etodolac
3 PM 20 mg propranolol
8 PM 300 mg etodolac In alternative embodiments, the beta blocker, e.g., the propranolol, is only given in the morning and afternoon (or at least before evening) to address the fact that it is known to interfere with the melatonin cycle, which influences sleep cycle and diurnal regulation, and propranolol has been shown to be important in suppressing cancer.

Figure 7:
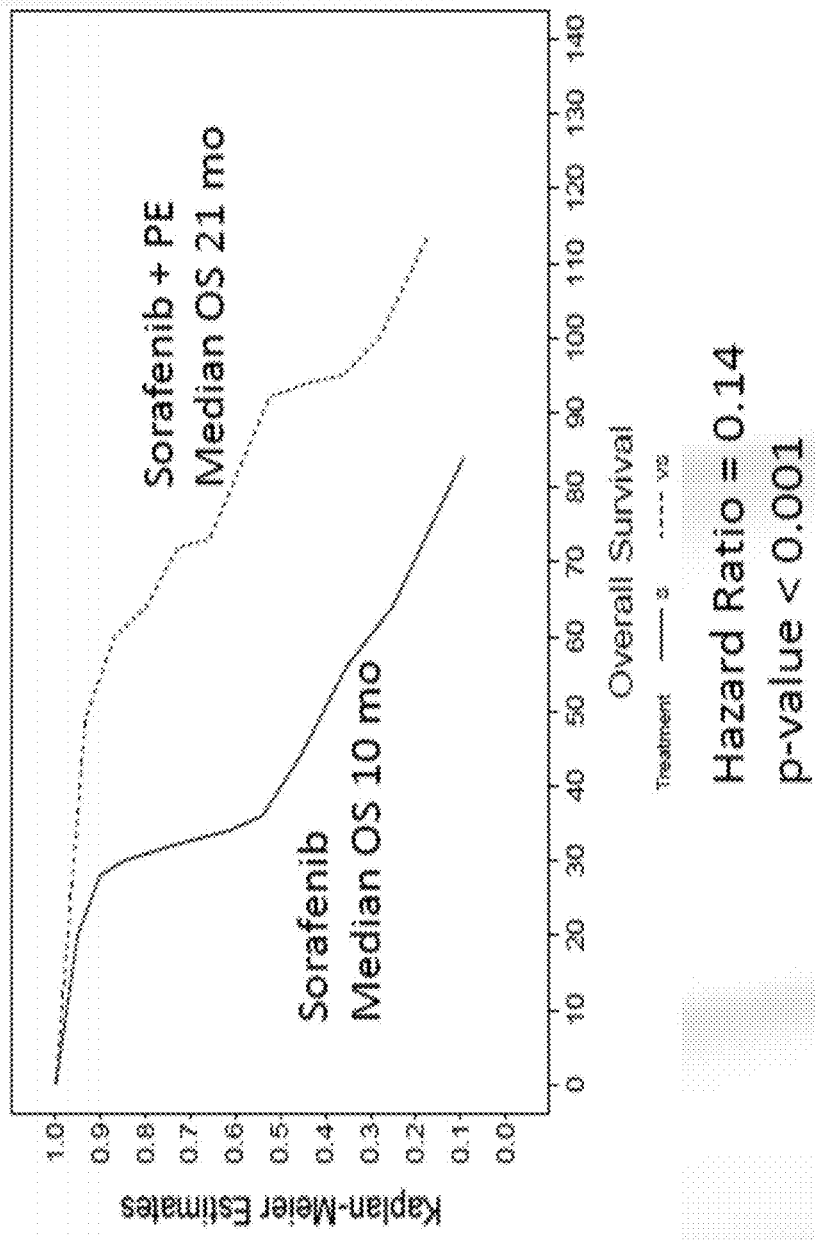
FIG. 7 graphically illustrates overall survival from a study described in detail in Example 1, below, where overall survival was adjusted for ECOG, graphically illustrated as Kaplan-Meier Estimates as a function of overall survival.

Results:

Twelve month survival was 25.0% (3/12) for Group S, 83.3% (10/12) for Group SPE and 41.7% (5/12) for group PE. Median survival for patients in Group S was 10 months, compared to 21 month for patients in Group SPE. Hand foot skin reaction, a major dose-limiting toxicity for sorafenib, was present at grade 2 or 3 67% of Group S and 17% of Group SPE. The treatment was well-tolerated with no unexpected adverse events. Survival is summarized in FIG. 7, which shows overall survival adjusted for ECOG, graphically illustrated as Kaplan-Meier Estimates as a function of overall survival, wherein the sorafenib only group had a median overall survival (OS) of ten months, and the exemplary therapeutic combination of sorafenib with beta blocker and NSAID (propranolol and etodolac) had a median OS of 21 months, and:

| 12 Month Survival | | | | |
|---|---|---|---|---|
| Group | N | Alive | Percent | P |
| S (sorafenib) | 12 | 3 | 25.0% | — |
| SPE (sorafenib + VT-122) | 12 | 10 | 83.3% | 0.004 |

Figure 8:
FIG. 8 graphically illustrates stabilization of weight loss as percent of patients gaining or losing weight, as described in detail in Example 1, below.

FIG. 8 graphically illustrates stabilization of weight loss as percent of patients gaining or losing weight, where in the sorafenib only group 50% of the patients had a greater than 50% loss in weight, and in the exemplary therapeutic combination of sorafenib with beta blocker and NSAID (propranolol and etodolac) group 42% of patients had a greater than 5% weight gain.

Figure 9:
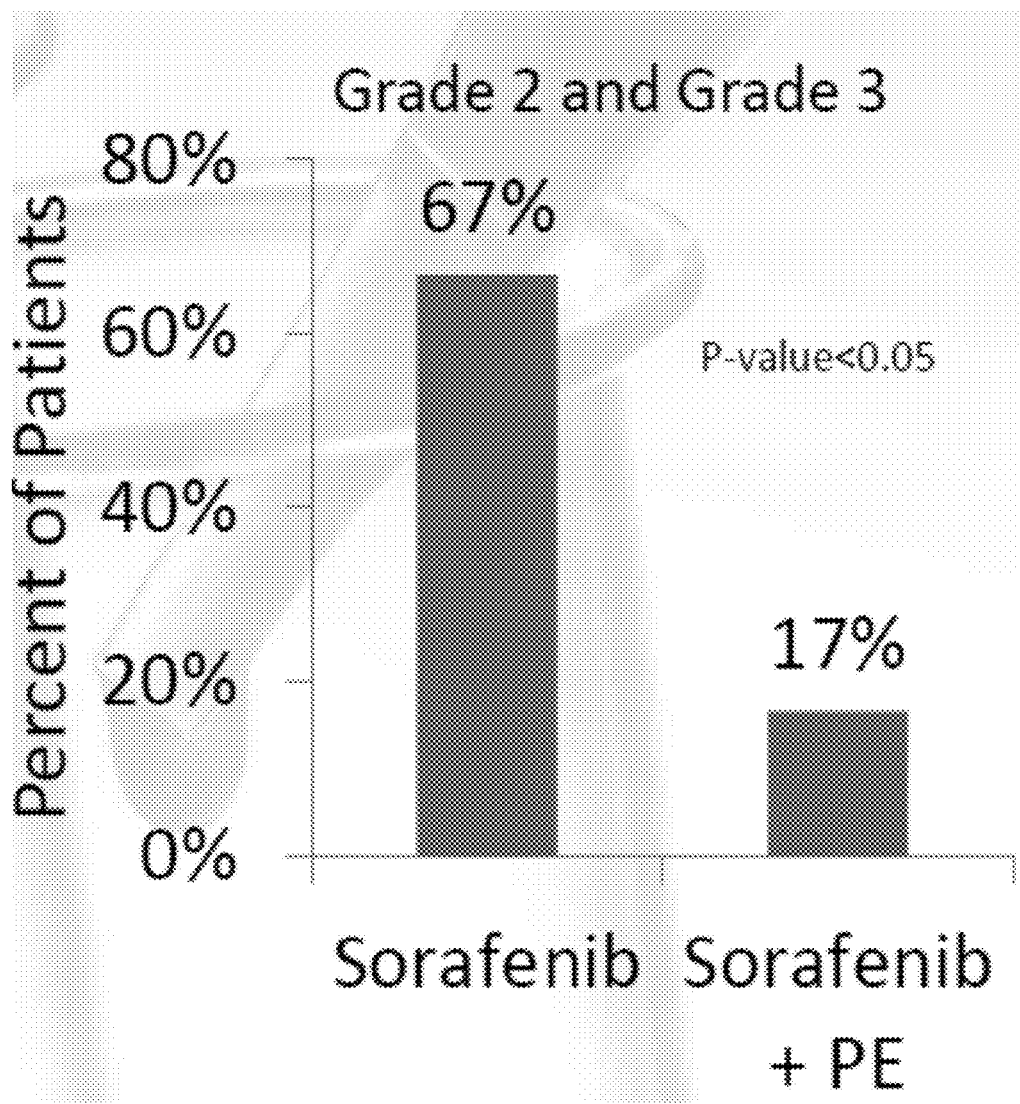
FIG. 9 graphically illustrates the incidence of hand-foot-skin reaction (HFS) as a percent of patients having grade 2 and grade 3 HFS, as described in detail in Example 1, below.

FIG. 9 graphically illustrates incidence of hand-foot-skin reaction (HFS) as a percent of patients having grade 2 and grade 3 HFS, where 67% of the patients if the sorafenib only group had HFS but only 17% of the patients in the exemplary therapeutic combination of sorafenib with beta blocker and NSAID (propranolol and etodolac) group had HFS.

Figure 10:
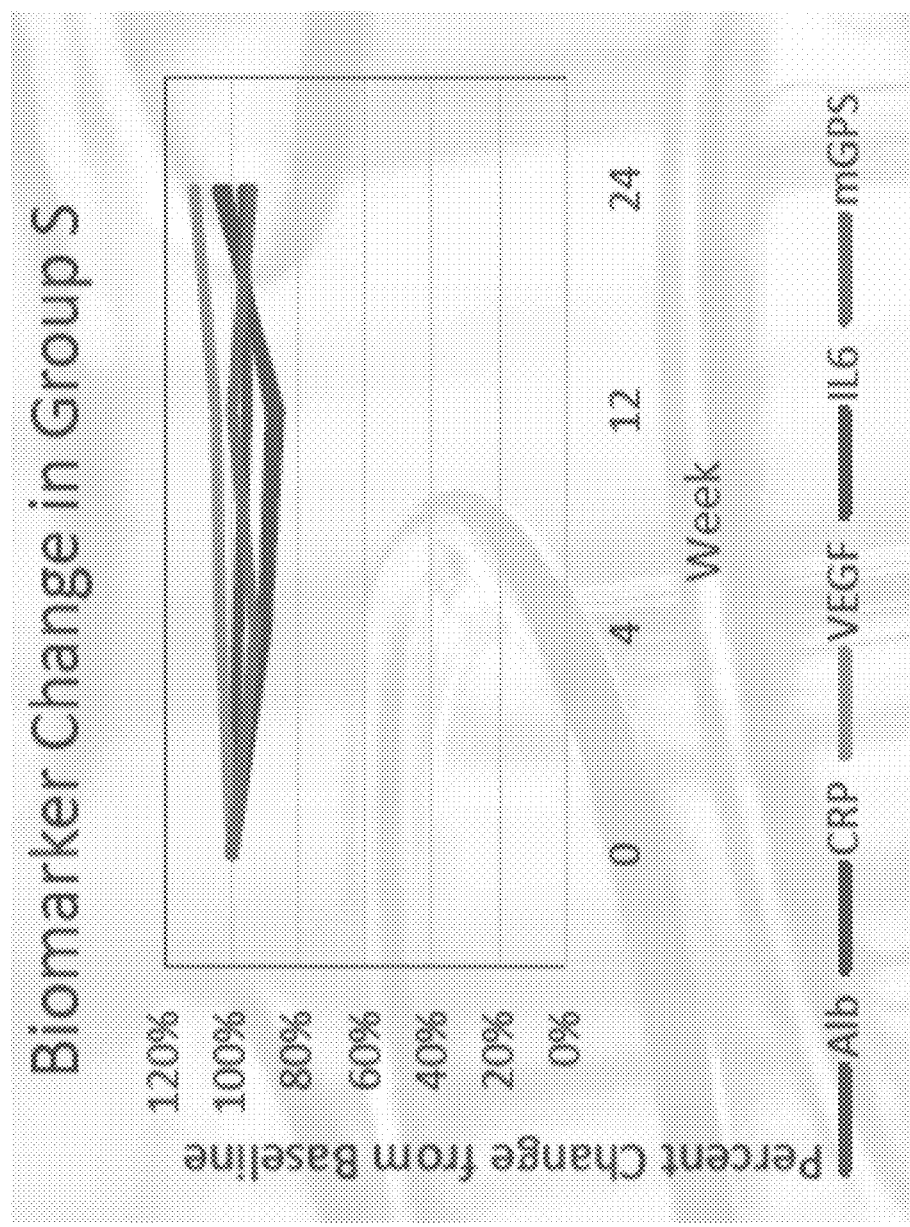
FIG. 10 graphically illustrates how the "Group S" patients with advanced HCC given the exemplary therapeutic combination of sorafenib with beta blocker and NSAID (propranolol and etodolac) group (SPE) had a greater reduction in inflammatory markers than in the sorafenib (S) alone group, the figure showing the percent change of biomarker from baseline.
Figure 11:
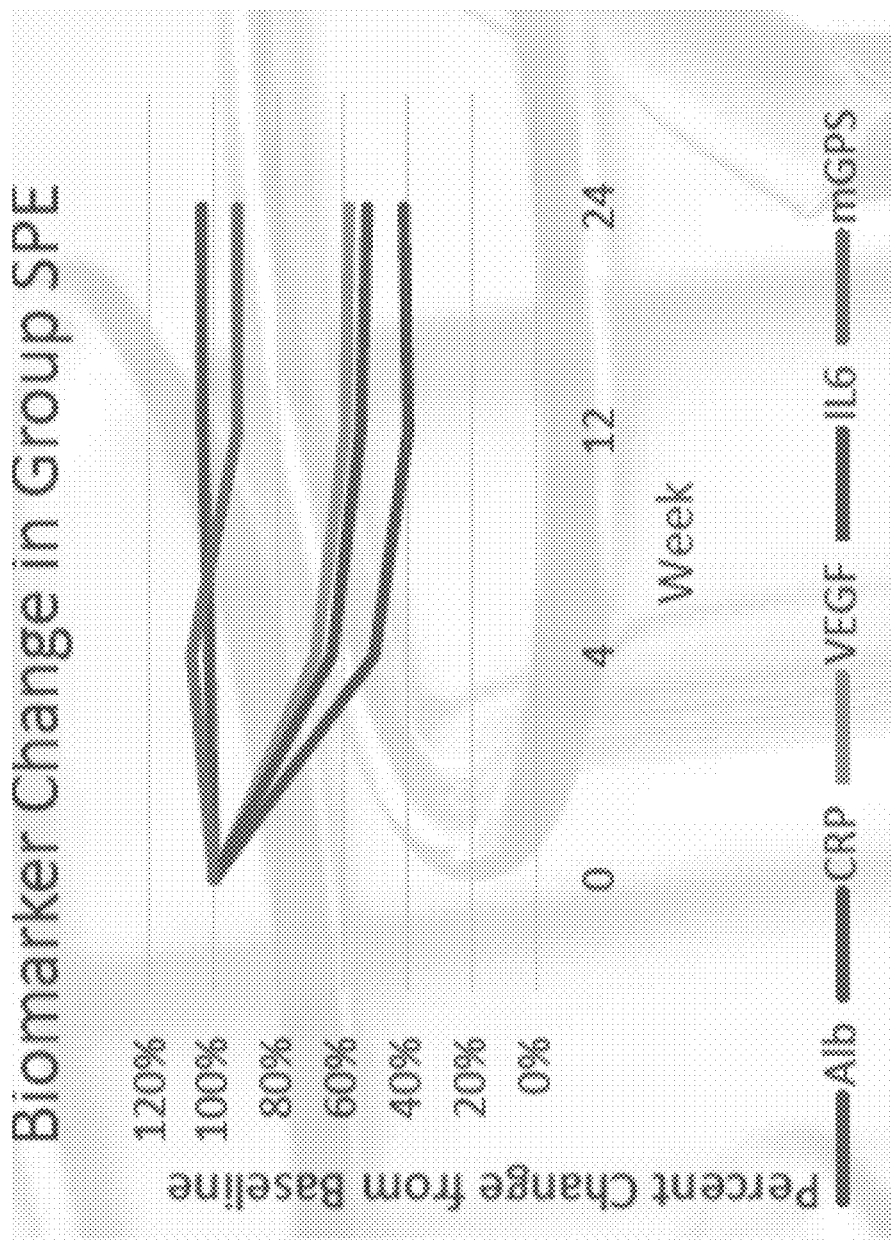
FIG. 11 graphically illustrates how the "Group SPE" patients with advanced HCC given the exemplary therapeutic combination of sorafenib with beta blocker and NSAID (propranolol and etodolac) group (SPE) had a greater reduction in inflammatory markers than in the sorafenib (S) alone group, the figure showing the percent change of biomarker from baseline.

FIG. 10 and FIG. 11 graphically illustrate how patients with advanced HCC in the exemplary therapeutic combination of sorafenib with beta blocker and NSAID (propranolol and etodolac) group (SPE) had a greater reduction in inflammatory markers than in the sorafenib (S) alone group.

Safety:

No unexpected or PE related serious adverse events; Reduction in incidence and severity of HFSR; No evidence of cardiac toxicity; No hypotension; Gastric pain was the same between groups.

Conclusions:

Twelve month survival was 25.0% (3/12) for Group S and 83.3% (8/12) and for Group SPE. Median survival for patients in Group S was 10 months, compared to 21 months for patients in Group SPE. Patients on SPE showed a significant reduction in HFSR and stabilization of weight. The treatment was well-tolerated with no unexpected adverse events. In summary, administration of PE one week prior to S significantly increased 12 month survival and overall survival in the ITT population while also reducing HFSR and stabilizing total body weight. No unexpected adverse reactions were seen.

A number of aspects of the invention have been described. Nevertheless, it will be understood that various modifications may be made without departing from the spirit and scope of the invention. Accordingly, other aspects are within the scope of the following claims.

What is claimed is:

1. A method for treating or ameliorating a hepatocarcinoma or a hepatocellular carcinoma, comprising: applying or administering to an individual in need thereof a therapeutic combination of therapeutic agents or drugs,
   wherein
   the therapeutic combination of therapeutic agents or drugs comprises:
   (a) a propranolol;
   (b) an etodolac; and
   (c) a 4-[4-[[4-chloro-3-(trifluoromethyl)phenyl]carbamoylamino]phenoxy]-N-methy-l-pyridine-2-carboxamide, or a sorafenib,
   wherein the therapeutic combination is administered in a chronodosed regimen comprising:
   Week 1:
   20 mg propranolol, 75 mg etodolac in the AM
   20 mg propranolol in the afternoon, or at about 3 PM
   300 mg etodolac in the PM;
   Week 2:
   (a)
   35 mg propranolol, 75 mg etodolac, 400 mg sorafenib in the AM
   25 mg propranolol at in the afternoon, or at about 3 PM
   600 mg etodolac in the PM, or
   (b)
   35 mg propranolol, 75 mg etodolac, 400 mg sorafenib in the AM
   25 mg propranolol at in the afternoon, or at about 3 PM
   600 mg etodolac, 400 mg sorafenib in the PM;
   Week 3:
   same as Week 2;
   Week 4
   35 mg propranolol,
   25 mg propranolol at in the afternoon, or at about 3 PM.

2. The method of claim 1, further comprising administering to the individual in need thereof
   an additional systemic anti-cancer or anti-tumor treatment.

3. The method of claim 1, wherein if patients cannot tolerate the propranolol or etodolac chronodosed regimen at week 2, then return to the Week 1 chronodose regimen.

4. The method of claim 1, wherein the therapeutic agents or drugs are formulated for oral administration.

5. The method of claim 4, wherein the therapeutic agents or drugs are packaged together in a blister card packaging system, a blister package, a lidded blister or a blister card or packet, a clamshell, a tray or a shrink wrap.

6. The method of claim 1, wherein the therapeutic agents or drugs are formulated as a powder, a spray, an aerosol, a pellet, a suppository, a lotion, a patch, an adhesive, a cream or an ointment.

7. The method of claim 1, wherein the therapeutic agents or drugs are packaged in dosages that match the chronodosing regimen.

8. The method of claim 1, wherein the therapeutic agents or drugs are formulated for administration intravenously (IV), parenterally, nasally, topically or locally, orally, or by liposome, implant or vessel-targeted nanoparticle delivery.

9. The method of claim 1, wherein the method further comprises administering to the individual in need thereof an anti-cancer or anti-tumor radiotherapy or a proton beam therapy.

10. A method for treating or ameliorating a hepatocarcinoma or a hepatocellular carcinoma, comprising: applying or administering to an individual in need thereof a therapeutic combination of therapeutic agents or drugs,
    wherein the therapeutic combination of therapeutic agents or drugs comprises:
    (a) a propranolol;
    (b) an etodolac; and
    (c) a 4-[4-[[4-chloro-3-(trifluoromethyl)phenyl]carbamoylamino]phenoxy]-N-methy-l-pyridine-2-carboxamide, or a sorafenib,
    wherein the therapeutic combination is administered in a chronodosed regimen comprising:
    (a) For about 1 week:
    20 mg propranolol, 75 mg etodolac in the AM
    20 mg propranolol in the afternoon, or at about 3 PM
    300 mg etodolac in the PM;
    (b) Followed by for between about 1 to three weeks:
    (1)
    35 mg propranolol, 75 mg etodolac, 400 mg sorafenib in the AM
    25 mg propranolol at in the afternoon, or at about 3 PM
    600 mg etodolac in the PM, or
    (2)
    35 mg propranolol, 75 mg etodolac, 400 mg sorafenib in the AM
    25 mg propranolol at in the afternoon, or at about 3 PM
    600 mg etodolac, 400 mg sorafenib in the PM;
    (3) Followed by no treatment for about 1 to 10 days; and
    (4) Followed by repeating (1), (2) and (3) for about 1, 2, 3, or 4 or more cycles.

11. The method of claim 10, wherein administering to the individual in need thereof further comprises administering an additional systemic anti-cancer or anti-tumor treatment.

12. The method of claim 10, wherein the therapeutic agents or drugs are formulated for oral administration.

13. The method of claim 12, wherein the therapeutic agents or drugs are packaged together in a blister card packaging system, a blister package, a lidded blister or a blister card or packet, a clamshell, a tray or a shrink wrap.

14. The method of claim 10, wherein the therapeutic agents or drugs are formulated as a powder, a spray, an aerosol, a pellet, a suppository, a lotion, a patch, an adhesive, a cream or an ointment.

15. The method of claim 10, wherein the therapeutic agents or drugs are packaged in dosages that match the chronodosing regimen.

16. The method of claim 10, wherein the therapeutic agents or drugs are formulated for administration intravenously (IV), parenterally, nasally, topically or locally, orally, or by liposome, implant or vessel-targeted nanoparticle delivery.

17. The method of claim 10, wherein the method further comprises administering to the individual in need thereof an anti-cancer or anti-tumor radiotherapy or a proton beam therapy.

18. The method of claim 1, wherein the sorafenib is NEXAVAR™.

19. The method of claim 2, wherein the additional systemic anti-cancer or anti-tumor treatment comprises administration of a drug, a biologic, a nutrient, an anti-cancer or anti-tumor dietary regimen, a radioactive agent, a tumor ablative agent.

20. The method of claim 4, wherein the therapeutic agents or drugs are formulated as a capsule, a geltab or a tablet.

21. The method of claim 10, wherein the sorafenib is NEXAVAR™.

22. The method of claim 11, wherein the additional systemic anti-cancer or anti-tumor treatment comprises administration of a drug, a biologic, a nutrient, an anti-cancer or anti-tumor dietary regimen, a radioactive agent, a tumor ablative agent.

23. The method of claim 12, wherein the therapeutic agents or drugs are formulated as a capsule, a geltab or a tablet.

* * * * *